United States Patent
Crivelli et al.

(10) Patent No.: US 8,141,844 B2
(45) Date of Patent: Mar. 27, 2012

(54) FLOW RATE ACCURACY OF A FLUIDIC DELIVERY SYSTEM

(75) Inventors: Rocco Crivelli, Neuchâtel (CH); Alec Ginggen, Plymouth, MA (US); Toralf Bork, Enges (CH)

(73) Assignee: Codman NeuroSciences Sàrl, LeLocle (CH)

( * ) Notice: Subject to any disclaimer, the term of this patent is extended or adjusted under 35 U.S.C. 154(b) by 364 days.

(21) Appl. No.: 12/255,666

(22) Filed: Oct. 22, 2008

(65) Prior Publication Data
US 2009/0140185 A1 Jun. 4, 2009

Related U.S. Application Data

(63) Continuation-in-part of application No. 11/259,413, filed on Oct. 26, 2005.

(51) Int. Cl.
*F16K 31/02* (2006.01)
(52) U.S. Cl. ............... 251/129.05; 251/129.06
(58) Field of Classification Search ............. 251/129.01, 251/129.05, 129.06
See application file for complete search history.

(56) References Cited

U.S. PATENT DOCUMENTS

| | | | |
|---|---|---|---|
| 365,477 A | 6/1887 | Kieley |
| 1,166,439 A | 1/1916 | Corbin |
| 1,374,571 A | 4/1921 | Hummel |
| 1,727,281 A | 9/1929 | Fulton |
| 1,800,995 A | 4/1931 | Gaunt |
| 2,239,169 A | 4/1941 | Franck |
| 2,493,449 A | 1/1950 | Fitch |
| 2,575,775 A | 11/1951 | Teeters |
| 2,599,872 A | 6/1952 | Slonneger |
| 2,613,056 A | 10/1952 | Hughes |
| 2,623,785 A | 12/1952 | Henchert |
| 2,715,009 A | 8/1955 | Beekley |
| 3,524,474 A | 8/1970 | McCormick |
| 3,746,036 A | 7/1973 | DuBois et al. |
| 3,759,294 A | 9/1973 | Kongelka |
| 4,221,219 A | 9/1980 | Tucker |
| 4,487,603 A | 12/1984 | Harris |
| 4,557,294 A | 12/1985 | Brunner |
| 4,584,980 A | 4/1986 | Weiger et al. |
| 4,673,391 A | 6/1987 | Kondo et al. |
| 4,714,234 A | 12/1987 | Falk et al. |
| 4,752,445 A | 6/1988 | Zell |

(Continued)

FOREIGN PATENT DOCUMENTS

EP  0387439  9/1990

(Continued)

OTHER PUBLICATIONS

Copending, co-owned U.S. Appl. No. 11/259,413.

(Continued)

*Primary Examiner* — John Fristoe, Jr.
(74) *Attorney, Agent, or Firm* — Cheryl F. Cohen, LLC

(57) ABSTRACT

Improving the accuracy of the flow rate of a valve in a fluidic delivery device in which a desired flow rate may be achieved by varying the duty cycle of the valve. The flow rate of fluid delivery from the valve over its lifetime is stabilized by minimizing the voltage OPENING time of the valve to account for valve and piezoelectric actuator drift. Also, the valve OPENING time of one or more fluidic parameters that impact on the flow rate delivery by the valve and differ among fluidic delivery devices is compensated to optimize the flow rate accuracy.

8 Claims, 15 Drawing Sheets

U.S. PATENT DOCUMENTS

| | | | |
|---|---|---|---|
| 4,944,659 A | 7/1990 | Labbe et al. | |
| 5,161,774 A | 11/1992 | Engelsdorf et al. | |
| 5,277,556 A | 1/1994 | Van Lintel | |
| 5,593,134 A * | 1/1997 | Steber et al. | 251/129.17 |
| 5,725,017 A | 3/1998 | Elsberry | |
| 6,095,175 A | 8/2000 | Miller | |
| 6,152,898 A | 11/2000 | Olsen | |
| 6,176,256 B1 | 1/2001 | Nakajima et al. | |
| 6,394,981 B2 | 5/2002 | Heruth | |
| 6,554,022 B2 | 4/2003 | Wakeman | |
| 6,685,164 B1 | 2/2004 | Koizumi | |
| 6,685,444 B2 | 2/2004 | Ogawa | |
| 7,070,577 B1 | 7/2006 | Haller | |
| 7,156,365 B2 * | 1/2007 | Fuller et al. | 251/129.04 |
| 2002/0179152 A1 | 12/2002 | Wakeman | |
| 2003/0100863 A1 | 5/2003 | Shekalim | |
| 2004/0041111 A1 | 3/2004 | Boecking | |
| 2005/0219302 A1 | 10/2005 | Vogeley | |
| 2006/0018770 A1 | 1/2006 | Baumann et al. | |
| 2007/0090321 A1 | 4/2007 | Bork | |

FOREIGN PATENT DOCUMENTS

| | | |
|---|---|---|
| EP | 0763368 | 3/1997 |
| EP | 1177802 A1 | 2/2002 |
| EP | 1582232 A1 | 10/2005 |
| EP | 1779888 A1 | 5/2007 |
| GB | 218782 A | 7/1924 |
| JP | 5344755 A | 12/1993 |
| JP | 6177449 A | 6/1994 |
| WO | WO 92/16247 | 10/1992 |
| WO | WO 9938551 A1 | 8/1999 |
| WO | WO 01/66173 | 9/2001 |

OTHER PUBLICATIONS

Copending, co-owned U.S. Appl. No. 11/096,369.

Commonly owned pending U.S. Appl. No. 12/255,662.

Commonly owned pending U.S. Appl. No. 11/259,413.

\* cited by examiner

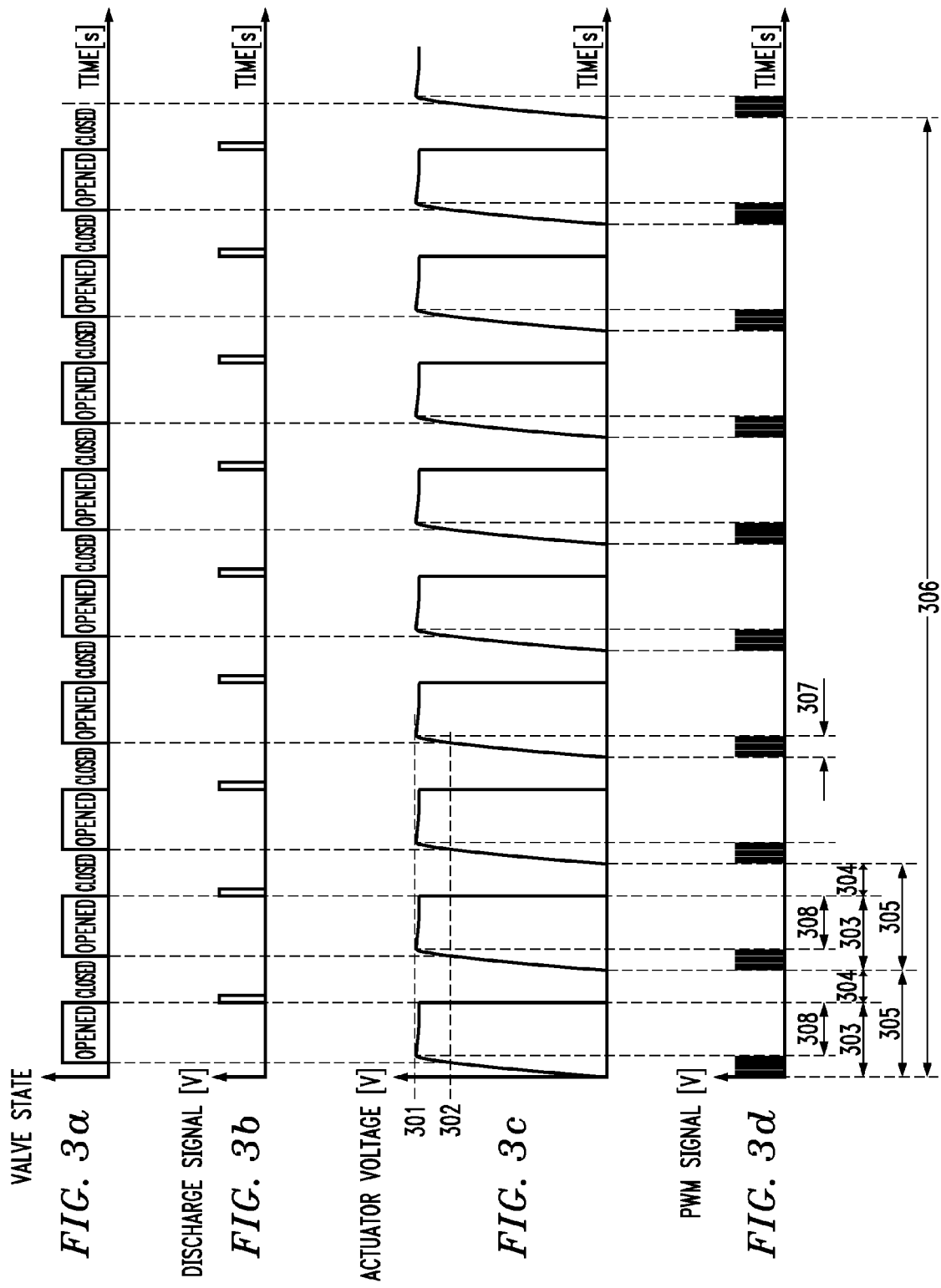

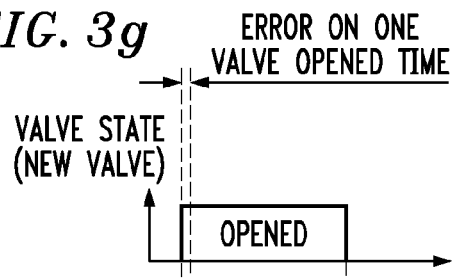
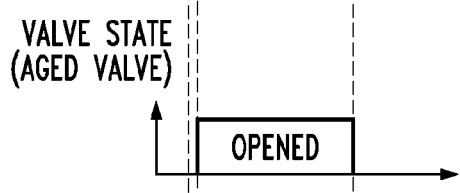
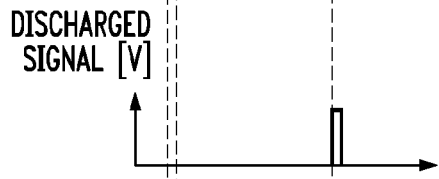
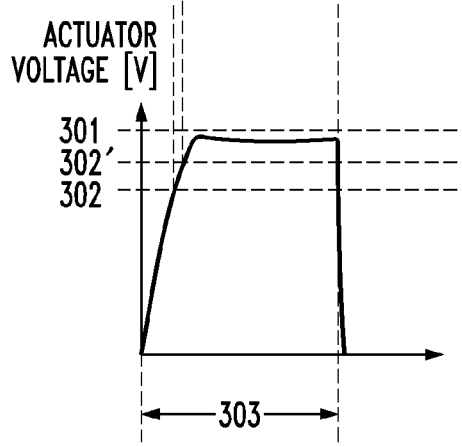
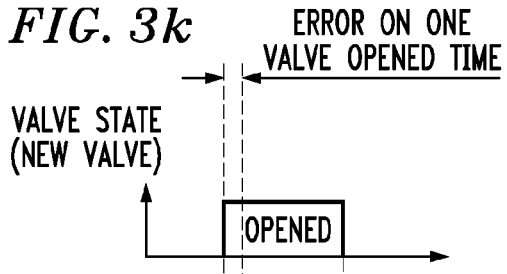
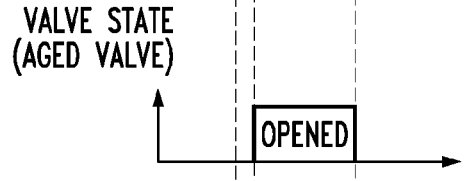
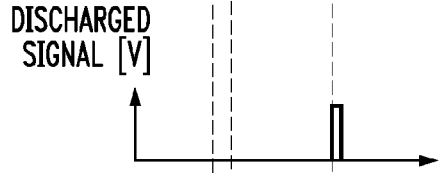
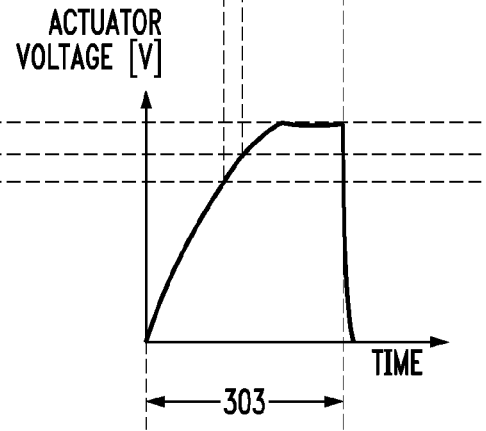

VALVE IS OPEN
THE BUBBLE IS DECOMPRESSED

VALVE CLOSES
THE BUBBLE IS COMPRESSED

VALVE IS CLOSED
THE BUBBLE IS COMPRESSED

US 8,141,844 B2

FLOW RATE ACCURACY OF A FLUIDIC DELIVERY SYSTEM

CROSS-REFERENCE TO RELATED APPLICATIONS

This application is a continuation-in-part of prior application Ser. No. 11/259,413, filed Oct. 26, 2005, which is herein incorporated by reference in its entirety.

BACKGROUND OF THE INVENTION

1. Field of the Invention

The present invention is directed to a system and method for improving the flow rate accuracy of a fluidic delivery system.

2. Description of Related Art

Fluidic delivery devices have widespread use in the medical field with the use of implantable drug infusion delivery devices for delivering a drug or other fluid to the body at specified flow rates over time. The implantable drug infusion delivery device is generally programmed via a control unit disposed external to the body and in communication with the implantable drug infusion delivery device via a communication interface, preferably a wireless communication interface such as RF telemetry. There are many types of drug infusion delivery devices or pumps such as peristaltic, bellows, piston pumps. U.S. Patent Application Publication No. 2007/0090321 A1 discloses one exemplary piston pump, which is herein incorporated by reference in its entirety.

With the advent of such technology, it is possible to program a specific drug profile over time to be dispensed or delivered from the implantable drug infusion delivery device. Such functionality may be used for dispensing a wide range of drugs such as pain medication or the delivery of insulin as well as many others. Despite the advantages associated with using an implantable drug infusion delivery device to automatically dispense a drug over time based on a programmed drug delivery profile, its efficacy depends on the ability of the implantable drug infusion delivery device to dispense the medication at a substantially constant flow rate on which the programmed drug delivery profile was based. Otherwise, if the flow rate of fluid dispensed by the drug infusion delivery device varies over time then the programmed drug delivery profile will result in either an underdosage or an overdosage. Any deviation in the drug dispensed may have unintended if not harmful, and in some cases life threatening, health effects for the patient.

It is therefore desirable to develop an improved system and method for stabilizing the flow rate of a fluidic delivery device over its lifetime and also to optimize the flow rate accuracy of a fluid delivered from a fluidic delivery device to compensate for one or more fluidic parameters that compromise the flow rate.

SUMMARY OF THE INVENTION

The present invention is directed to a system and method for improving the accuracy of the flow rate of a valve in a fluidic delivery device in which a desired flow rate may be achieved by varying the duty cycle of the valve. The flow rate of fluid delivery from the valve over its lifetime is stabilized by minimizing the voltage OPENING time of the valve to account for valve and piezoelectric actuator drift. Also, the valve OPENING time of one or more fluidic parameters that impact on the flow rate delivery by the valve and differ among fluidic delivery devices is compensated to optimize the flow rate accuracy.

BRIEF DESCRIPTION OF THE DRAWING

The foregoing and other features of the present invention will be more readily apparent from the following detailed description and drawings of illustrative embodiments of the invention wherein like reference numbers refer to similar elements throughout the several views and in which:

FIG. 1b is a cross-sectional view of the valve assembly of FIG. 1a;

FIG. 3a is an exemplary graphical representation of the actual valve OPENED and valve CLOSED timing of the valve assembly in FIG. 1b over time;

FIG. 3b is an exemplary graphical representation of the discharge signal for discharging of the piezoelectric actuator;

FIG. 3c is an exemplary graphical representation of the piezoelectric actuator voltage;

FIG. 3d is an exemplary graphical representation of the PWM charge input signal to the charge pump circuitry in FIG. 4 wherein the PWM charge input signal has been divided into 20 PWM units each having its associated PWM parameters;

FIGS. 3g-3j represent waveforms depicting valve state, discharge signal and actuator voltage signal associated with an exemplary first valve OPENING time;

FIGS. 3k-3n represent waveforms depicting valve state, discharge signal and actuator voltage signal associated with an exemplary second valve OPENING time greater than the first valve OPENING time depicted in FIGS. 3g-3j;

DETAILED DESCRIPTION OF THE INVENTION

Figure 1A:
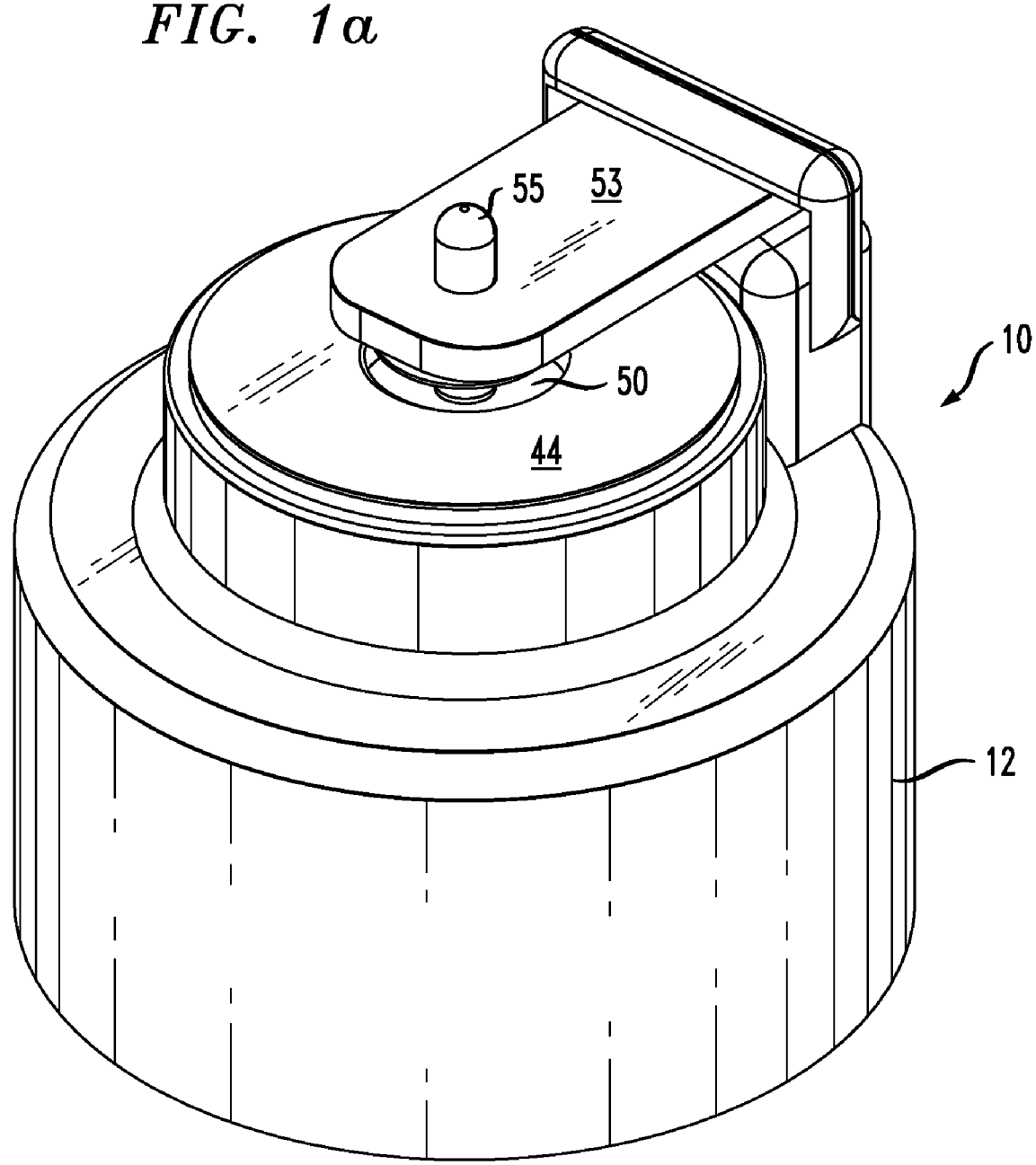
FIG. 1a is a perspective view of a valve assembly 10 for a fluidic system.
Figure 1B:
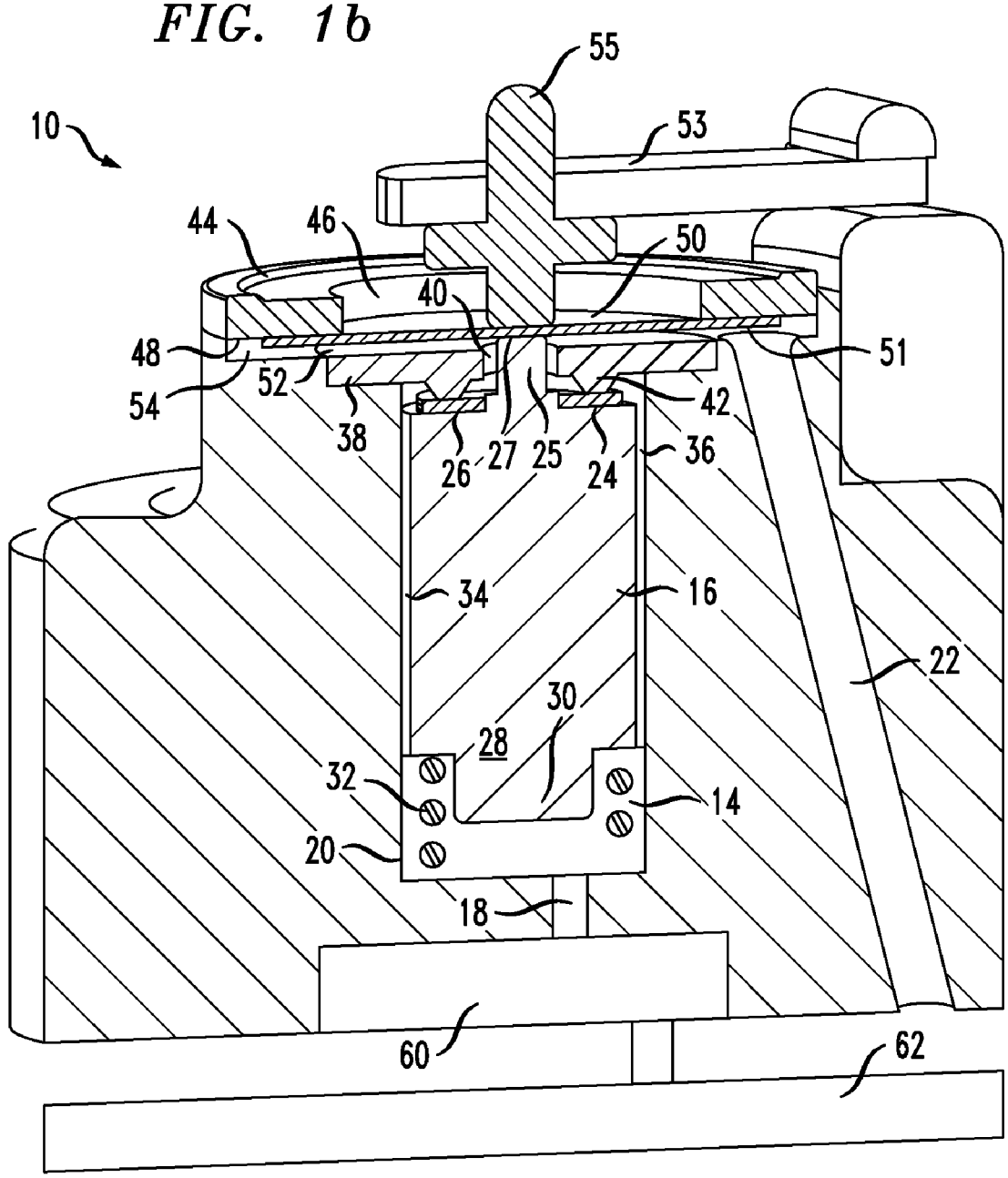

FIGS. 1a and 1b depict a valve assembly 10 for use in a fluidic system, e.g., implantable drug infusion delivery system. Valve assembly 10 has a body 12 which defines a bore 14 that is sized and shaped to slidably receive a piston 16, as shown in the cross-sectional view of FIG. 1b. Body 12 further includes an inlet passage 18 that provides fluid communication between a fluid reservoir 62 and a lower end 20 of bore 14. In addition, body 12 includes an outlet passage 22 for transporting fluid from the valve assembly 10 (when the valve is in an OPEN state) to a conduit that delivers the fluid to a desired site of interest.

In this exemplary valve structure or assembly 10, piston 16 is positioned within bore 14 and includes an upper sealing end 24 that supports a disc-shaped seal 26. Piston 16 has an opposite lower end 28, which includes a downwardly-directed boss 30 sized and shaped to receive one end of a compression spring 32. In addition, piston 16 has defined therein a circumferentially disposed spiral groove 34 (positioned along the sidewall and extending substantially the length of the piston 16) providing fluid communication between the lower end 20 of bore 14 (and inlet passage 18) and upper sealing end 24 of piston 16. Fluid entering the lower end 20 of bore 14 (under pressure from the reservoir 62) freely advances between the piston 16 and the bore 14 via spiral groove 34.

As shown in FIG. 1b, spring 32 is positioned between lower end 28 of piston 16 and the lower end 20 of bore 14. Spring 32 biases piston 16 and disc-shaped seal 26 upwardly towards an upper end 36 of bore 14.

Securely attached (i.e., preferably hermetically sealed) to body 12 and positioned over upper end 36 of bore 14 is a contact disc 38 that is preferably made from a rigid material such as a metal. Contact disc 38 has a central opening 40 defined therein and an integrally formed, downwardly-directed contact ridge 42. Contact ridge 42 is formed preferably concentrically to central opening 40 and sized and shaped to fit within bore 14, as shown in FIG. 1b. Contact disc 38 is positioned so that contact ridge 42 aligns with disc-shaped seal 26. As piston 16 is pushed upwardly by spring 32, disc-shaped seal 26 is pressed into a sealing contact with circular contact ridge 42 thereby closing the valve assembly 10, as described in greater detail below.

Projecting from upper sealing end 24 of piston 16 is a substantially axially-aligned contact pin 25. Contact pin 25 is adapted to be displaceable within substantially central opening 40 defined in contact disc 38 while an upper contact surface 27 extends and remains above contact disc 38. Downward displacement of contact pin 25 causes piston 16 to separate disc-shaped seal 26 from sealing contact of contact ridge 42 of contact disc 38 thereby opening the valve assembly.

Securely affixed to body 12 (i.e., preferably hermetically sealed) and positioned over upper end 36 of bore 14 and contact disc 38 is a portal support ring 44 which includes a central opening 46 and defines a lower surface 48. Attached to the lower surface 48 and covering the central opening 46 is a thin, flat coin-like, flexible membrane 50 positioned above an upper surface 52 of contact disc 38 a predetermined distance so that a collection space 54 is defined therebetween.

Membrane 50 is generally made from a relatively strong resilient metal such as titanium and is brazed or welded to the lower surface 48 of portal support ring 44. Similarly, portal support ring 44 is brazed to body 12 so that piston 16, disc-shaped seal 26, spring 32, inlet passage 18, outlet passage 22, and contact disc 38 all define a "wet side" relative to membrane 50 (lower side) and are all hermetically sealed within the valve body 12 yet isolated from everything located above and outside the valve body 12 by a space which defines a "dry side" relative to membrane 50. Upper surface 27 of contact pin 25 abuts against a lower surface 51 of membrane 50. Spring 32 biases contact pin 25 into firm contact with lower surface 51 of membrane 50.

The valve assembly 10 is opened and closed repeatedly at a predetermined frequency by applying the mechanical displacement generated by a piezoelectric actuator or piezo crystal 53 (in response to an applied electrical signal) to move piston 16 axially up and down. An actuation pin 55 is used to connect the piezoelectric actuator 53 to contact pin 25 indirectly through membrane 50, as described below. Actuation pin 55 is substantially axially aligned with contact pin 25.

In operation of the above described valve assembly 10, fluid (e.g., a drug in liquid form) is supplied to inlet passage 18 under pressure from a reservoir 62, but regulated by a fluidic pressure regulator or fluidic restrictor 60 such as a fluidic chip. Fluid enters lower end 20 of bore 14. When piston 16 is forced downwardly within bore 14 against the action of spring 32 fluid from the reservoir 62 passes through the fluidic pressure regulator 60 and into the inlet passage 18 moving past piston 16 by way of groove 34 to the top of piston 16. Downward displacement of piston 16, in turn, causes disc-shaped seal 26 to separate from contact ridge 42 thereby allowing fluid (still under regulated pressure) to pass through central opening 40 defined in contact disc 38 and enter the collection space 54. Any fluid within collection space 54 will be forced into outlet passage 22 and eventually directed to a desired site of interest (such as a desired treatment area of a patient's body).

Downward movement of piston 16 is controlled by applying a specific electrical signal to the piezoelectric actuator 53 that as a result thereof deforms with a slight downward displacement. This slight downward movement is transferred to the contact pin 25 through the actuation pin 55 and flexible membrane 50. Therefore, the particular electric signal applied to the piezoelectric actuator 53 will indirectly control the opening of the valve assembly 10 and therefore the amount and flow rate of fluid passing from inlet passage 18 to the outlet passage 22.

The flow rate of the fluid being dispensed from the outlet passage 22 is adjustable by varying the ratio of the valve OPENED time/valve CLOSED time (ratio of the duration of time in which the valve is in respective OPENED and CLOSED states) of the valve assembly 100 by means of the piezoelectric actuator 53. Pressurized reservoir 62 is fluidly connected to the fluidic regulator or restrictor 60. The outlet of the flow regulator or restrictor 60 is, in turn, fluidly connected via an inlet passage 18 to the bore 14 in which piston 16 is displaceable thereby opening and closing the valve. While in an OPENED state fluid is permitted to pass through the valve assembly 10 and dispensed via the outlet passage 22. When the valve assembly 10 is in an OPENED state, the fluidic restrictor 60 and the differential pressure across it define a constant flow rate at the outlet passage 22 of the fluidic delivery system.

The constant flow rate dispensed from the valve assembly can be adjusted, as desired, by varying the ratio of the valve OPENED time to the valve CLOSED time hereinafter referred to as the duty cycle. During a predetermined period of time or duration (hereinafter referred to as a "block") the valve assembly opens once (the piezoelectric actuator is charged) and the valve closes once (the piezoelectric actuator is discharged). Knowing the predetermined block duration (e.g., 400 seconds), the flow rate for the valve assembly can be determined based on the duration of the valve OPENED time versus the valve CLOSED time.

Figure 2A:
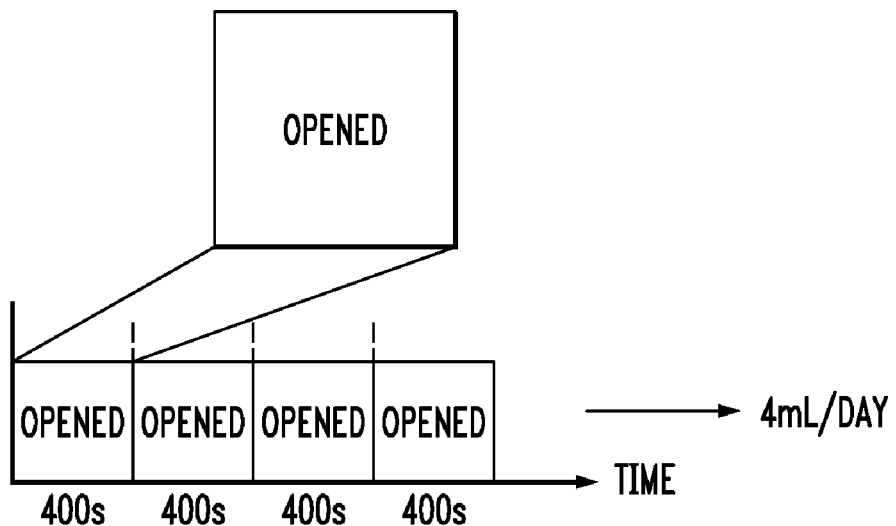
FIGS. 2a-2c show different exemplary flow rates for a valve assembly having a block of 400 seconds by varying the duty cycle in accordance with the present invention.
Figure 2B:
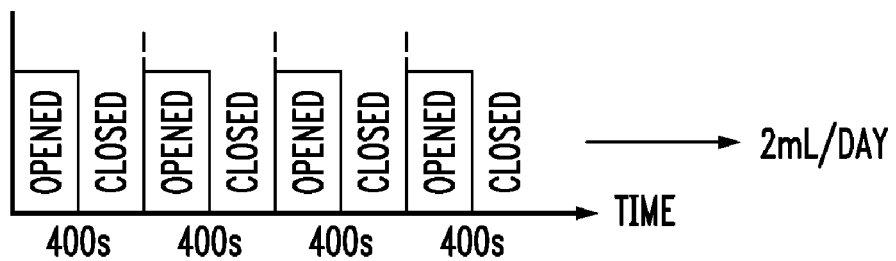
Figure 2C:
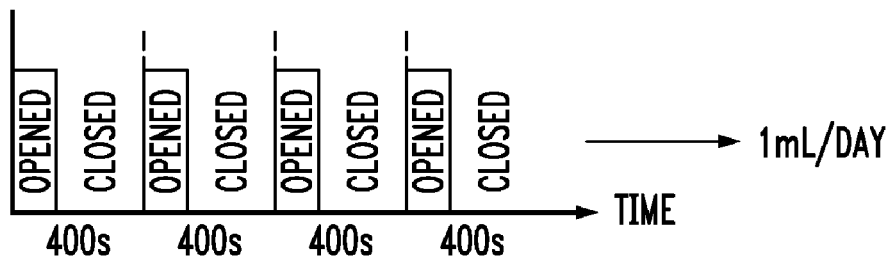

FIGS. 2a-2c depict different flow rates, e.g., 4 ml/day, 2 ml/day and 1 ml/day, respectively. A maximum constant flow rate of 4 ml/day is represented in the first example shown in FIG. 2a in which for each 400 second block the valve OPENED time is the virtually the full 400 seconds, while the valve CLOSED time is extremely short, almost zero (as denoted by the enlarged view of the first 400 second block). The second example, shown in FIG. 2b shows for each 400 second block the valve OPENED time and the valve CLOSED time are equally 200 seconds duration each. This would result in a flow rate half that of the maximum flow rate (e.g., 4 ml/day shown in FIG. 2a) for a constant flow rate of 2 mL/day. A third example is depicted in FIG. 2c in which the valve OPENED time is for 100 seconds while the valve CLOSED time is 300 seconds. The third duty cycle example will produce a constant flow rate of 1 mL/day. By varying the duty cycle (i.e., the ratio of the valve OPENED time to the valve CLOSED time) a desired constant flow rate of fluid dispensed from the valve may be realized.

Figure 3E:
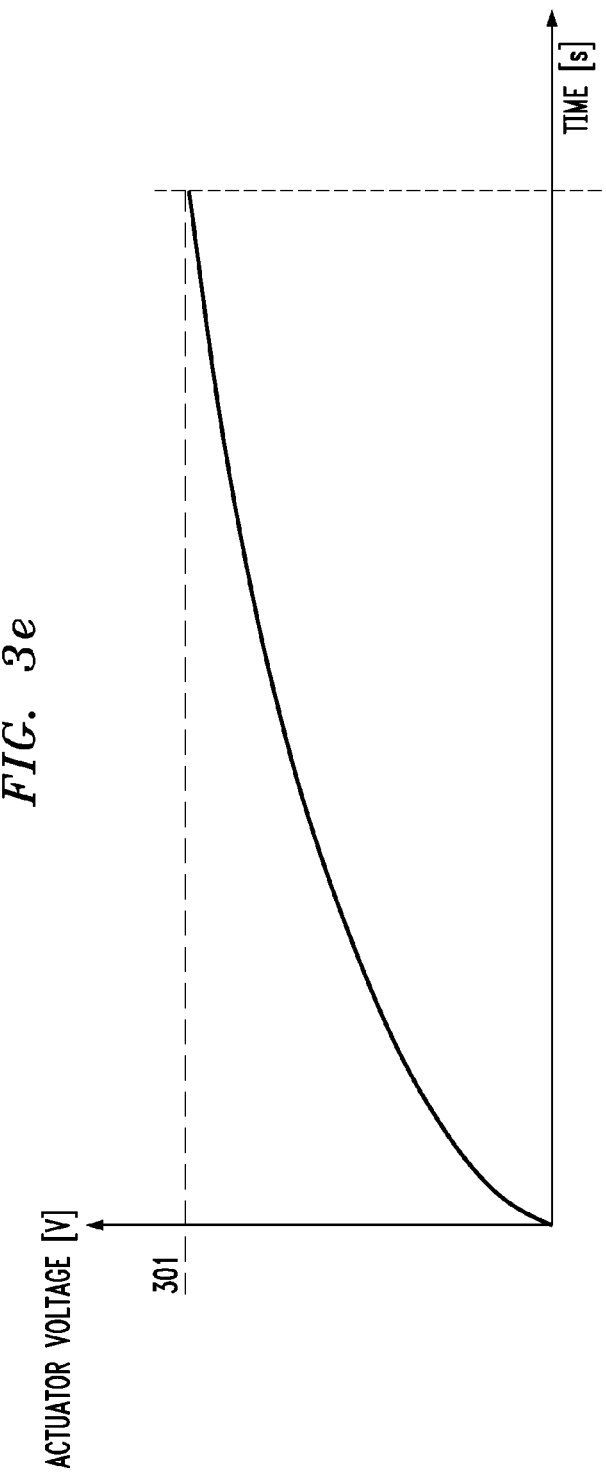
FIG. 3e is an enlarged exemplary graphical representation of the piezoelectric actuator voltage from FIG. 3b during a single PWM charge input signal comprising 20 PWM units.

FIG. 3a is an exemplary graphical representation of the opening and closing over one hour of valve assembly 10 in FIGS. 1a and 1b. There are a total of 9 blocks within one hour depicted in FIG. 3a, each block being 400 seconds. The smallest time interval over which the valve can be programmed by a user is 1 hour increments. Each 400 second block comprises a valve OPENED time and a valve CLOSED time of equal duration (e.g., 200 seconds). By way of example, the maximum flow rate defined by the flow restrictor 110 and the differential pressure across it is 2 ml/day. This example is merely for illustration purposes and any one or more of the parameters, may be selected as desired, including: (i) the duration or time period of the block (e.g., 400 seconds), (ii) minimum programming period of time (for example, one hour), (iii) maximum flow rate in a 24 hour period, (iv) valve OPENED time, and (v) valve CLOSED time.

Valve assembly 10 is a mechanical device that forms a fluid channel capable of being either opened or closed by a piezoelectric actuator 53. When actuated the piezoelectric actuator 53 bends and moves the plunger or piston 16 downward via actuation pin 55. As a result, the valve opens. A predetermined threshold voltage of 60 V (as denoted by line 301 in FIG. 3c) is needed to be applied across the piezoelectric actuator in order to open the valve assembly 10. The voltage across the piezoelectric actuator 53 is supplied by power supply (e.g., a battery) and associated charge pump circuitry an example of which is shown in FIG. 4.

Figure 4:
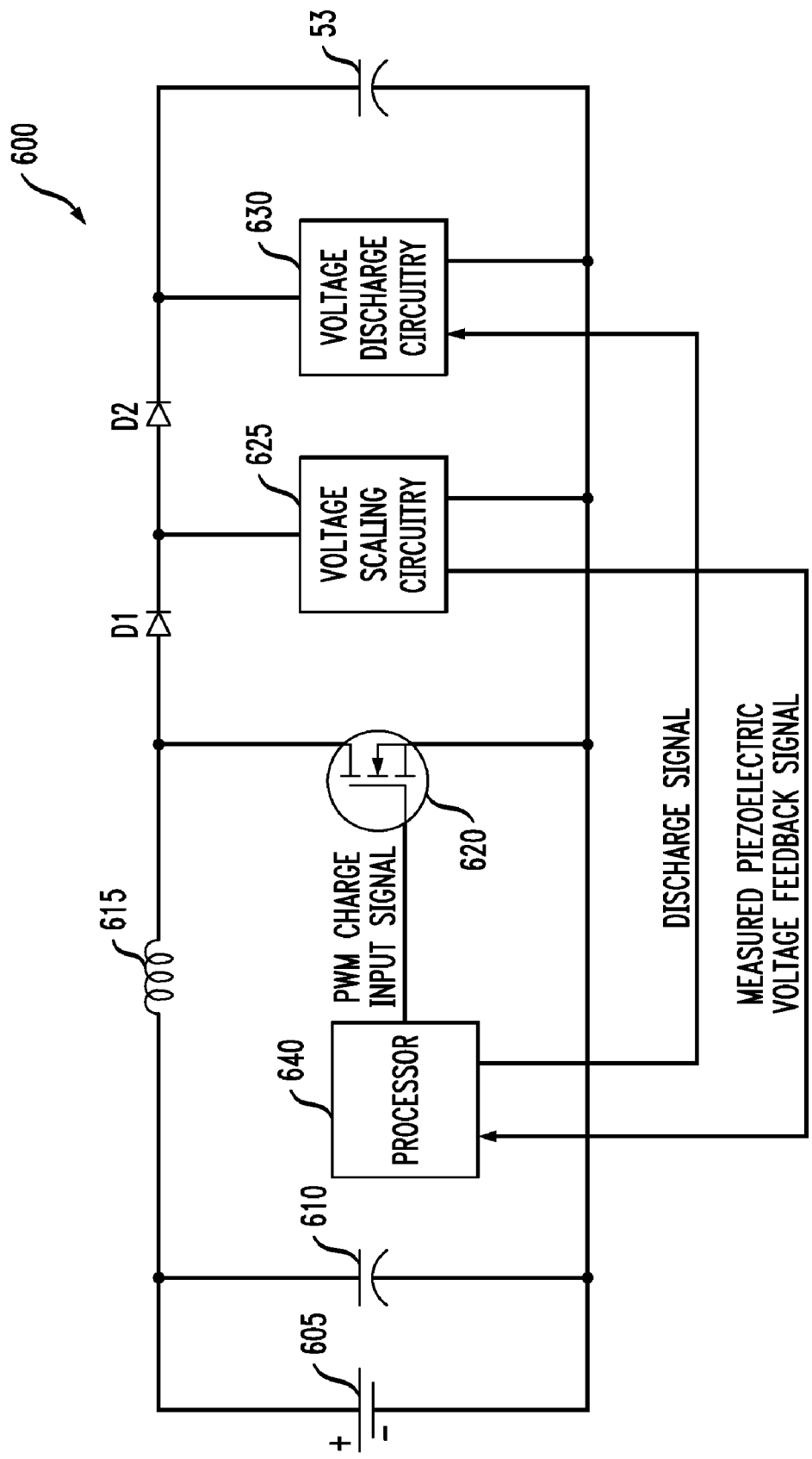
FIG. 4 is an exemplary schematic circuit diagram for generating a PWM charge input signal to achieve a predetermined threshold voltage of 60V across the piezoelectric actuator in FIG. 2 and open the valve.

Circuitry 600, in FIG. 4, is used to charge the piezoelectric actuator 53 to the predetermined threshold voltage of 60V that, in turn, opens the valve assembly 10 (in FIG. 1b). Power supply 605, for example a battery is used to power circuitry 600. The battery may be a rechargeable battery or a non-rechargeable battery. As represented by the shaded PWM charge input signal 307 in FIG. 3d, the piezoelectric actuator 53 is charged once every block (e.g., 400 seconds) regardless of the flow rate, therefore the lifetime of the power supply is independent of the flow rate. A capacitor 610 is connected in parallel with power supply 605. Transistor 620, for example a Field Effect Transistor (FET) is periodically switched ON and OFF in response to receiving a Pulse Width Modulated (PWM) charge pump input or driving signal generated by processor 640 to allow energy received from the power supply 605 and stored in an inductor 615 to charge the piezoelectric actuator 53.

Voltage Scaling Circuitry 625 scales down the relatively high measured voltage or charge stored by the piezoelectric actuator 53, preferably by a factor of 40, and generates a Measured Piezoelectric Voltage Feedback Signal that is received as input to the processor 640. A comparison is made by an analog comparator comprising processor 640 between the scaled down Measured Piezoelectric Voltage Feedback Signal and a similarly scaled down predetermined stored reference voltage of 1.2V (representing the predetermined threshold voltage of 60V scaled down by the same factor of 40 as that of the Measured Piezoelectric Voltage Feedback Signal) for actuating the piezoelectric actuator 53. If the scaled down Measured Piezoelectric Voltage Feedback Signal is less than 1.2V then the PWM charge pump input signal is generated causing the transistor 620 which receives it to switch ON and OFF and allow the stored charge in inductor 615 to be applied to the piezoelectric actuator 53. The Measured Piezoelectric Voltage Feedback signal is continuously monitored until it reaches 1.2V at which point processor 640 triggers an interrupt that cuts off the PWM charge pump input signal causing transistor 620 to switch OFF permanently thereby opening the circuit and preventing the flow of energy from the power supply 605 to the inductor 615. Accordingly, energy from the power supply 605 is only consumed during charging of the piezoelectric actuator 53 until reaching the predetermined threshold voltage of 60V. Once the valve is open (i.e., the piezoelectric actuator is charged to the predetermined threshold voltage of 60V) it is maintained opened (i.e., the piezoelectric actuator substantially retains its charge with relative small leakage over time (represented by the drop in voltage over the time represented by reference element 308 in FIG. 3d) due to relatively low leakage diodes D1 and D2) without requiring energy. At the end of the valve OPENED time (represented by each "OPENED" block in FIG. 3a), processor 640 generates a Disable Signal or Discharge Signal (shown in FIG. 3b) that is received as input by Voltage Discharge Circuitry 630 to discharge the charge built up across the piezoelectric actuator 53 from the predetermined threshold voltage of 60V (represented by reference element number 301) down to the valve OPENING voltage 302 that differs among fluidic delivery devices. Thus, the only negligible energy expended to discharge the piezoelectric actuator 53 and close the valve is the power required by the processor to generate the discharge pump signal and the energy dissipated by the transistor when switching its state.

The input of the charge pump circuitry is a PWM signal, such as the exemplary PWM signal shown in FIG. 3d. The output of the charge pump circuitry is the voltage applied across the piezoelectric actuator 53 as shown in FIG. 3c. It will take a predetermined period of time represented by reference element 307, referred to as rise time, for the voltage applied across the piezoelectric actuator 53 to attain the predetermined threshold voltage of 60V necessary to open the valve 115.

Over the lifetime of the valve assembly the valve OPENING voltage (reference element 302 in FIG. 3c) for a particular valve will increase due to drift of the piezoelectric actuator behavior. For instance, initially at the time of implantation, a valve may have a valve OPENING voltage of 55V and after the passage of a period of time, for example, several years, the valve OPENING voltage may rise to 57V. Variation in the valve OPENING voltage over the lifetime of the valve assembly will result in undesirable deviation in the accuracy of the programmed flow rate of the fluid being dispensed from the valve.

Despite the variation in valve OPENING voltage, the accuracy of the flow rate of fluid delivered from the fluidic delivery device may be stabilized or maintained over its lifetime by minimizing the valve OPENING time (i.e., the time it takes to the charge applied across the piezoelectric actuator to go from 0V to the opening voltage 302) to insure that the valve opens quickly. FIGS. 3g-3n illustrate this concept by depicting two different valve OPENING times. A first exemplary valve OPENING time is shown in FIGS. 3g-3j, while a second exemplary valve OPENING time is shown in FIGS. 3k-3n. The valve OPENING time in FIGS. 3k-3n is greater than that shown in FIGS. 3g-3j. As a result, the slope of the waveform in FIGS. 3k-3n is smaller (i.e., less steep) than that shown in FIGS. 3g-3j. Over time the valve OPENING voltage (reference element 302 in FIGS. 3j and 3n) will increase due to drift of the valve and piezoelectric actuator as represented by reference element 302'. At the valve OPENING voltage 302', the valve OPENED time in FIGS. 3g, 3k is reduced to that shown in FIGS. 3h, 3l, respectively, thereby compromising the accuracy of the flow rate delivered by the valve. Initially, the deviation or error due to reduced valve OPENED time resulting from this increase in valve OPENING voltage may be negligible, but over the lifetime of the valve OPENING voltage will continue to rise and eventually may result in a significant underdosage in the amount of fluid delivered. The relatively large valve OPENING time of the example in FIGS. 3k-3n reduces the valve OPENED time from that shown in FIG. 3k to that shown in FIG. 3l by an amount identified as "Error on one Valve OPENED time" (FIG. 3k). It has been recognized that reducing or minimizing the valve OPENING time (as represented by the graphical waveform in FIGS. 3g-3j in comparison to that shown in FIGS. 3k-3n) minimizes any reduction in valve OPENED time, as identified by the smaller "Error on one Valve OPENED time" shown in FIG. 3g compared to that in FIG. 3k. It is therefore desirable to minimize the valve OPENING time in order to minimize the reduction in valve OPENED time resulting from an increase in valve OPENING voltage over the lifetime of the valve to stabilize the flow rate.

The valve OPENING time can be minimized by dividing the PWM charge input signal for driving the charge pump into multiple PWM units, with each PWM unit applying for that duration of time its own associated or corresponding set of PWM parameters (e.g., frequency, duty cycle, and duration for which the PWM charge input signal should be generated (transistor ON time/transistor OFF time)). It is contemplated and within the scope of the present invention for each of the multiple PWM units to be equal or non-equal, as desired. There is an optimum number of PWM units that may be determined for the particular piezoelectric actuator for minimizing the valve OPENING time. On the one hand, if the number of PWM units is less than the optimum number of PWM units then the minimum valve OPENING time will not be realized. On the other hand, if the optimum number of PWM units is exceeded, no further reduction in valve OPENING time will be realized.

Figure 3F:
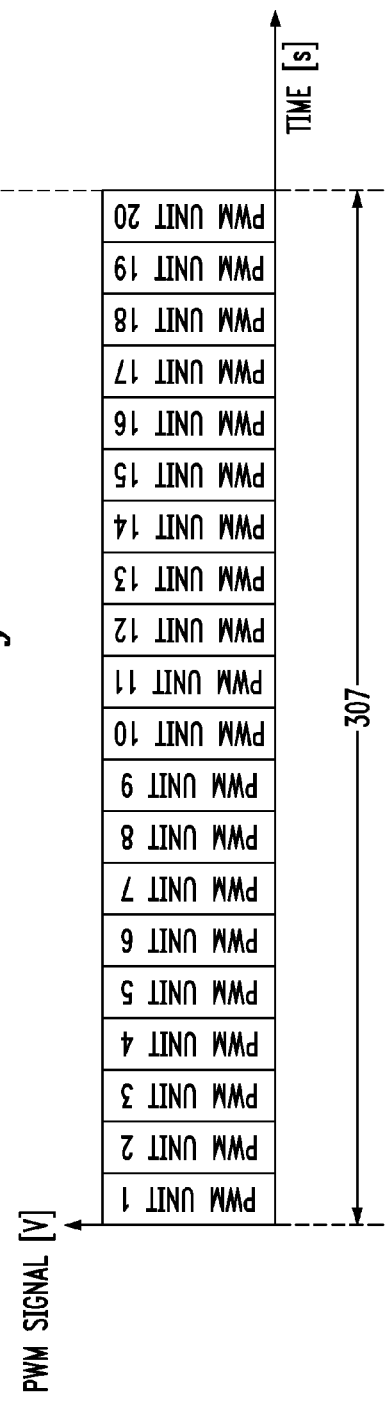
FIG. 3f is an enlarged exemplary graphical representation of a single PWM charge input signal comprising 20 PWM units.

An exploded view of a single PWM charge input signal (reference element 307 from FIG. 3d) is shown in FIG. 3f. In the example shown in FIG. 3f, the PWM charge input signal is divided into 20 PWM units each having is own associated PWM parameters. The 20 PWM units together for a single block are referred to as a PWM group (PWM charge input signal). At the beginning of each block (e.g., 400 second duration block) the PWM charge input signal is generated to drive the charge pump. The graphical representation shown in FIG. 3d shows the PWM charge input signal driving the charge pump until the voltage applied across the piezoelectric actuator 53 reaches the 60V predetermined threshold voltage (reference element 301 in FIG. 3c) necessary to displace the piezoelectric actuator and thus open the valve 115. When the voltage applied across the piezoelectric actuator 53 reaches the 60V predetermined threshold voltage the PWM charge input signal is cut off or ended by the processor 640 (FIG. 4). At the end of the valve OPENED time in FIG. 3a, a discharge signal is generated (FIG. 3b) by the processor 640 and received by the Voltage Discharge Circuitry 630 causing the voltage stored across the piezoelectric actuator 53 to drop from 60V to the valve OPENING voltage (reference element number 302 in FIG. 3c).

Figure 5:
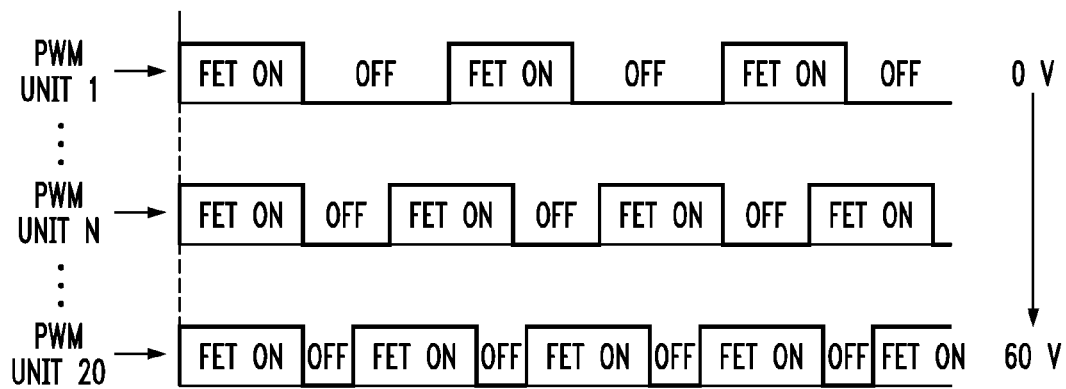
FIG. 5 shows an exemplary single PWM charge input signal generated for a single block of 400 seconds duration at a constant power supply voltage, wherein the PWM charge input signal is subdivided into 20 PWM units and varying the OFF time of the transistor in FIG. 4 while the transistor ON time remains constant.
Figure 6:
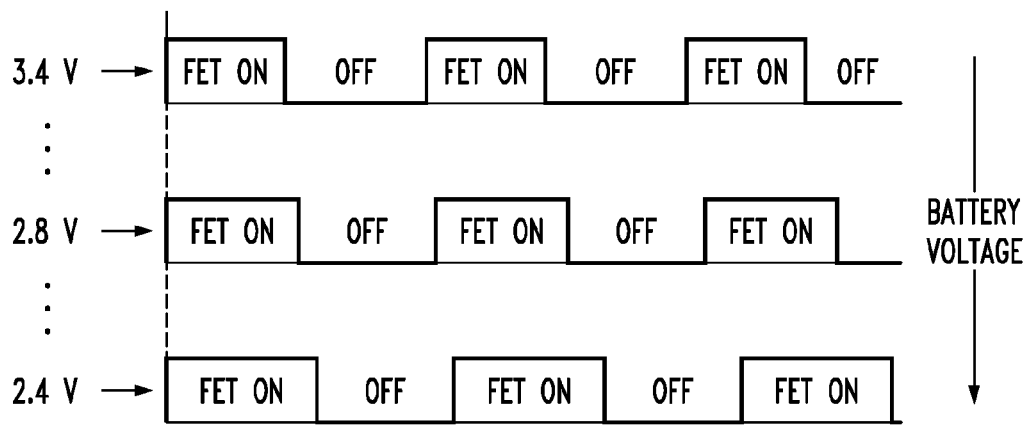
FIG. 6 shows exemplary PWM units over a period of time (e.g., several years) for depicting a decreasing power supply voltage, wherein the ON time of the transistor in FIG. 4 is varied while the transistor OFF time remains constant.

In still another improvement of the present invention, to further optimize valve OPENING time the transistor ON time and/or OFF time for each PWM unit of a PWM charge input signal may be adjusted as represented by the examples shown in FIGS. 5 and 6. For a constant battery voltage, the time duration for each block (e.g., 400 seconds) is fixed and the transistor ON time (period of time for which the transistor 620 is ON) is also fixed, however, the transistor OFF time (period of time for which transistor 620 is OFF) may vary among the different PWM units in a particular PWM group (i.e., a particular PWM charge input signal). Since the maximum current drawn from the power supply 605 is limited, the transistor ON time is fixed to limit the current drawn. The charge pump draws current from the power supply 605 when the PWM charge input signal is generated. The transistor OFF time duration must be sufficient to insure complete transfer of charges from the inductor 615 that stores the charge to the piezoelectric actuator 53. Since the time to transfer charge from the inductor 615 to the piezoelectric actuator 53 depends on the charge already stored in the piezoelectric actuator 53 at any given time, the transistor OFF time varies among PWM units within a particular PWM group.

In addition, over time, for example, the passing of several years, the power supply voltage will decrease and thus the amount of charge built across the inductor 615 will also decrease. It is therefore advantageous to vary the transistor ON time when the power supply voltage changes in order to optimize the valve OPENING time. Similarly, the transistor OFF time may be adjusted in order to allow sufficient time for charge transfer from the inductor 615 to the piezoelectric actuator 53, as described in the preceding paragraph.

FIG. 5 shows an exemplary PWM charge input signal (PWM group) generated for a single block of 400 seconds duration at a constant power supply voltage. The exemplary PWM charge input signal (PWM group) shown is divided into 20 PWM units of equal duration (PWM unit-1, . . . unit-N, . . . unit-20). The first PWM unit (PWM unit-1) is generated at the beginning of the 400 second block when the charge across the piezoelectric actuator 53 is 0V. With each subsequent PWM unit the voltage across the piezoelectric actuator increases until the predetermined threshold voltage (e.g., 60V) is applied to the piezoelectric actuator with the last PWM unit (PWM unit-20). All PWM units have a constant or fixed transistor ON time duration in which the PWM charge input signal is generated. The transistor ON time duration is limited by the current drawn from the power supply (e.g., battery) and therefore remains constant or fixed among all PWM charge input signals (PWM groups) and all PWM units within a particular PWM charge input signal (PWM group).

Each PWM unit has a fixed transistor OFF time duration in which the PWM charge input signal is not generated, however, the transition OFF time duration may vary among PWM units in a particular PWM group. As seen in FIG. 5, the transistor ON time for all PWM units is constant or fixed. The transistor OFF time duration is constant in any particular PWM unit such as within PWM unit-1, unit-N or unit-20. However, the transistor OFF time duration varies among PWM unit-1, unit-N and unit-20. It is clearly shown in FIG. 4 that the transistor OFF time duration is reduced from PWM unit-1 to PWM unit-20. This adjustment in the transistor OFF time duration of the PWM signal in any particular PWM unit takes into account the fact that the charge stored in the piezoelectric actuator is built up over time. As previously mentioned, the time necessary to transfer charge from the inductor 615 to the piezoelectric actuator 53 decreases as the charge stored in the piezoelectric actuator 53 increase. Accordingly, the transistor OFF time duration representing the time needed to transfer the charge from the inductor 615 to the piezoelectric actuator 53 may be reduced.

FIG. 6 shows exemplary PWM units over a period of time (e.g., several years) for depicting a decreasing power supply voltage. Note that in contrast to that shown in FIG. 5, the PWM units illustrated in FIG. 6 do not represent PWM units within a single PWM group. Instead, what is represented is three PWM units at different instances of time over several years. Since the power supply voltage decreases over relatively long periods of time (e.g., several years) the different PWM units shown illustrate merely snap shots in time in which the battery voltage decreases relative to that of an earlier in time PWM unit. In this example during the time intervals between the PWM units depicted the battery voltage remains constant or fixed. Referring to FIG. 6, the PWM units will be addressed from top to bottom. The battery voltage measurement at the time of the top PWM unit was 3.4V. At some point in time thereafter, the measured battery voltage dropped to 2.8V corresponding to the intermediate PWM unit. After the duration of some period of time thereafter, a battery voltage of 2.4V was measured at the time of the bottom PWM unit. The transistor OFF time remains constant or fixed among all PWM groups and all PWM units within a particular PWM group. However, the transistor ON time is adjusted to account for decreasing power supply voltage over time. Specifically, the transistor ON time duration increases as the power supply voltage decreases. The reasoning for this is because since the power supply voltage decreases over time then the transistor ON time must increase in order to allow the same amount of energy relative to when the power source was fully charged to flow from the power supply 605 to the inductor 615 and subsequently to the piezoelectric actuator 53. In summary, a longer transistor ON time is required when the power supply 605 is not fully charged in order to transfer the same amount of energy from the power supply 605 to the inductor 615 and subsequently to the piezoelectric actuator 53 then would be transferred from a power supply 605 having a greater voltage and by using the same transistor ON time.

The two concepts presented separately in FIGS. 5 and 6 may be combined wherein when the power supply voltage remains constant or fixed the transistor OFF time for a particular PWM unit is adjusted, while the transistor ON time for a particular PWM unit is adjusted when the power supply voltage decreases.

Thus far, the accuracy of the flow rate has been maintained or stabilized for a particular fluidic delivery device in which the flow rate may vary over time due to such factors as: (i) mechanical drift over time, (ii) deformation of the seal with usage over time, and (iii) depletion of energy provided by the power supply. Accordingly, the previously described adjustments to the valve OPENING time maintains or stabilizes the flow rate accuracy for any given fluidic delivery device.

It is also recognized that the flow rate accuracy may be affected by parameters that differ from one fluidic delivery device to another. The flow rate accuracy may be dependent on any number of one or more factors (hereinafter collective referred to as "fluidic parameters") such as: (i) the compliance effect, (ii) the maximum flow rate for the given fluidic delivery device, (iii) the pressure on the fluid in the reservoir which is dependent on the temperature (temperature-pressure relationship of reservoir fluid), (iv) valve OPENING time (time for the charge applied across the piezoelectric actuator to go from OV to the valve OPENING voltage, e.g., reference element 302 in FIG. 3*c*), and (v) valve CLOSING time (time required to discharge the charge stored across the piezoelectric actuator from the 60V predetermined threshold voltage (reference element 301 in FIG. 3*c*) to the valve OPENING voltage (reference element 302 in FIG. 3*c*)). Accordingly, it is desirable to optimize the accuracy of the flow rate of fluid delivery by compensating for differences among fluidic delivery devices with respect to any one or more of these fluidic parameters. Each of these fluidic parameters will be addressed separately.

Referring once again to FIG. 1*b*, the contact disc 38 in the valve assembly 10 is positioned so that contact ridge 42 aligns with the disc-shaped seal 26. As piston 16 is pushed upwardly by compression spring 32, disc-shaped seal 26 is pressed into a sealing contact with circular contact ridge 42 thereby closing the valve assembly. When the valve is closed, the elevated or higher pressure from the reservoir 62 compresses the seal 26 downward toward the lower end 20 of bore 14. If the seal 26 was not made of a compressible material, the volume of fluid delivered by the fluidic delivery system would correspond to the graphical representation shown in FIG. 7. It is represented by the graphical waveform in FIG. 7 that when the valve is in an OPEN state a constant flow rate (denoted by a graphical waveform having a substantially constant slope) of fluid is delivered. On the other hand, while the valve is in a CLOSED state, a fixed or unchanging flow rate is experienced (as denoted by the substantially horizontal waveform). The waveform in FIG. 7 transitions directly from a substantially horizontal waveform to a constant flow rate as represented by that portion of the waveform having a constant positive slope.

Figure 7:
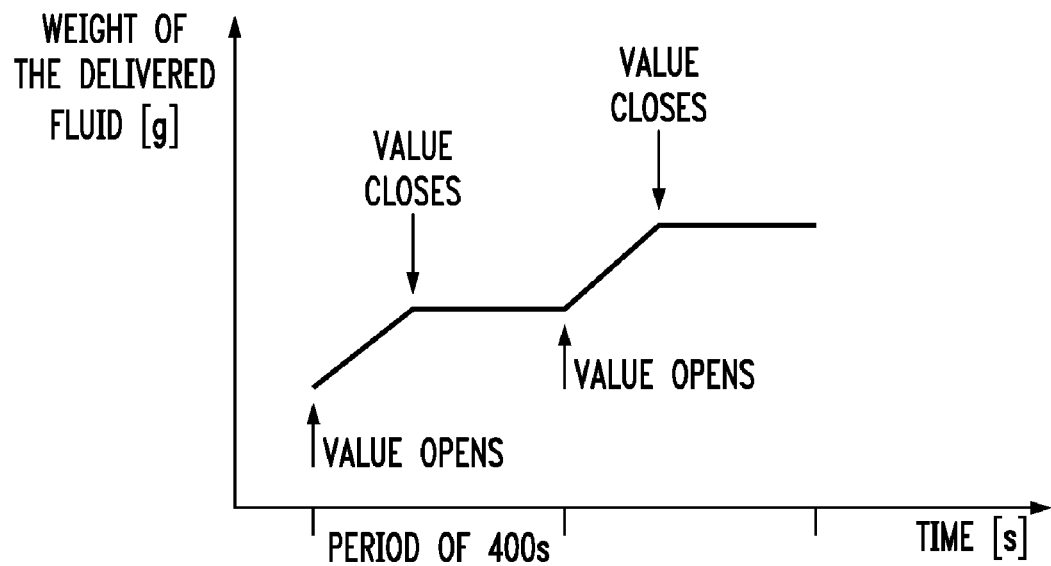
FIG. 7 is a graphical representation of the weight of fluid delivered by a fluidic delivery device over time without taking into consideration the compliance effect of the seal.

However, seal 26 is made of a compressible material and hence FIG. 7 fails to take into consideration the fluid dispensed from the valve when transitioning from the CLOSED state to the OPENED state due to what is referred to as the compliance effect of the seal. Every time the valve assembly transitions from a CLOSED state to an OPENED state there is a transition period before realizing a constant flow rate. This transition period is denoted by the substantially vertical line (segment "3") shown in FIG. 8 and hereinafter referred to as a "compliance effect." This "compliance effect" occurs because the seal 26 is made from a compressible material, e.g., silicon.

Figure 9A:
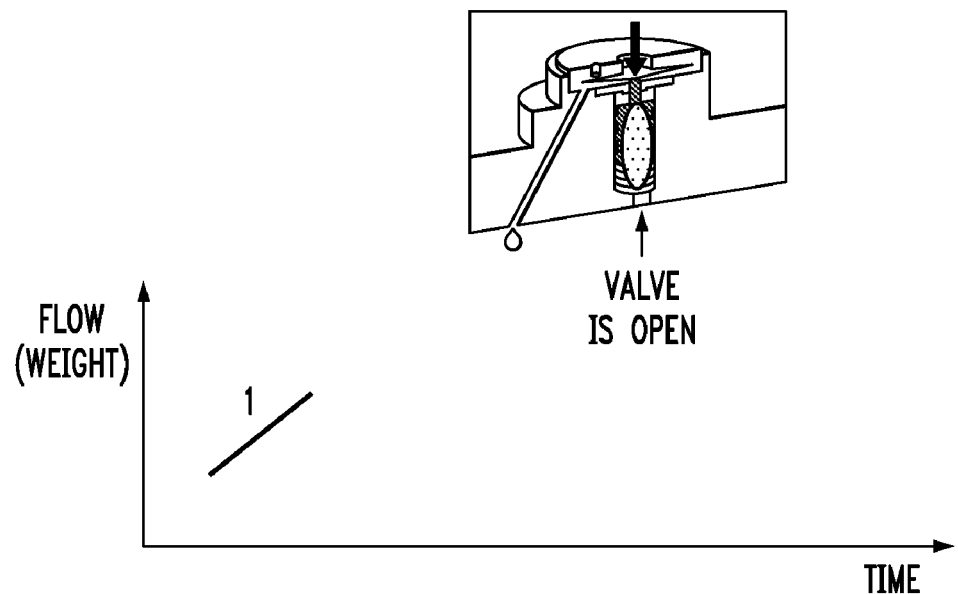
FIGS. 9a-9g show as an illustrative example of the compliance effect on an air bubble trapped in a valve as it opens and closes.
Figure 9B:
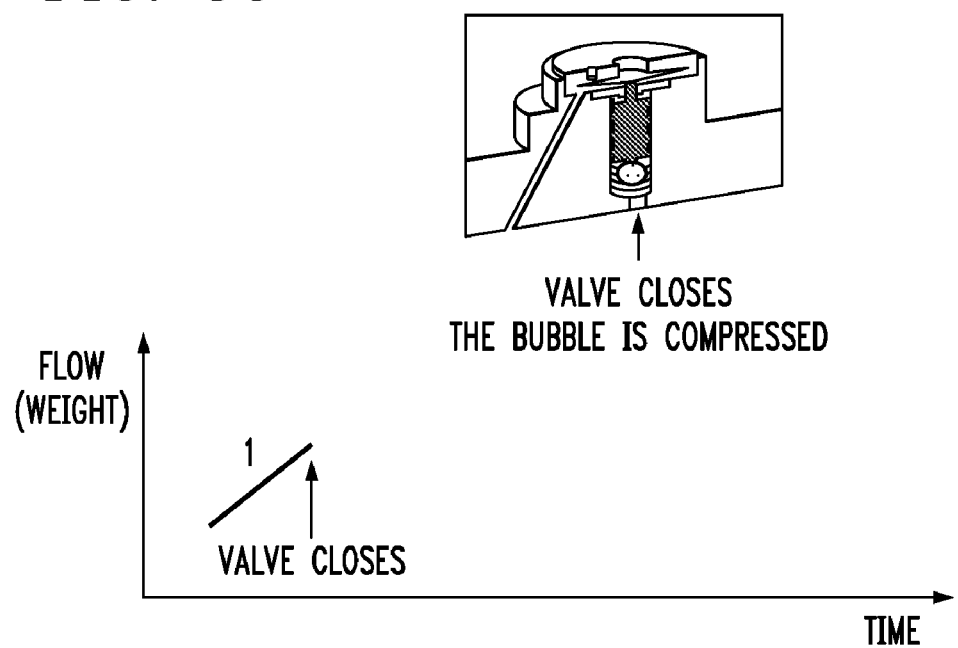
Figure 9C:
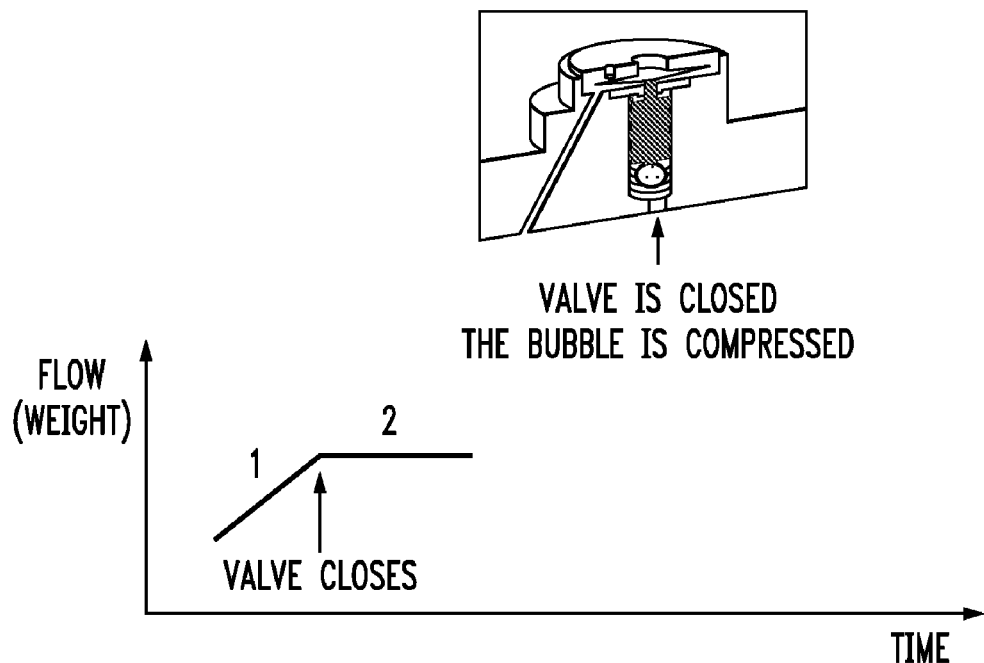
Figure 9D:
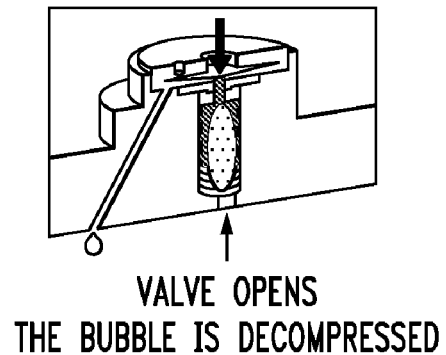
Figure 9D:
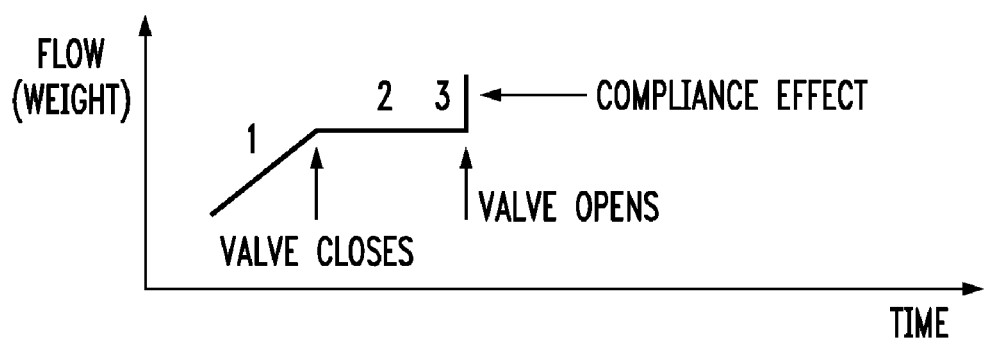
Figure 9E:
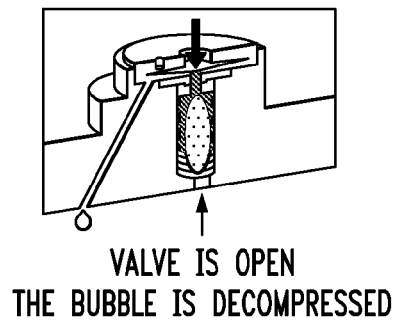
Figure 9E:
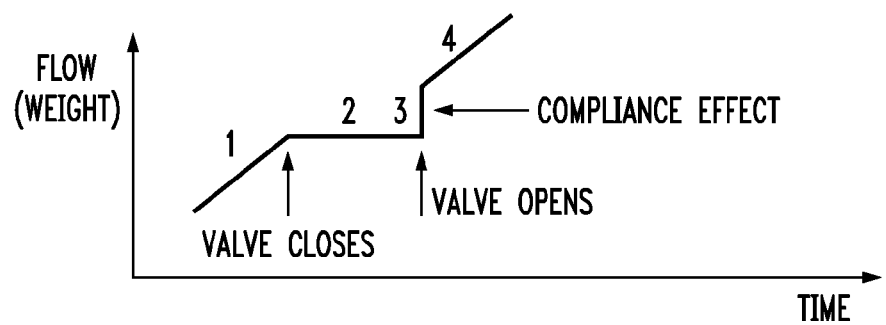
Figure 9F:
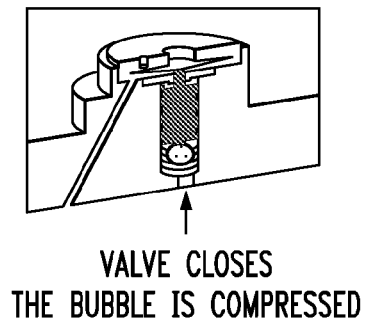
Figure 9F:
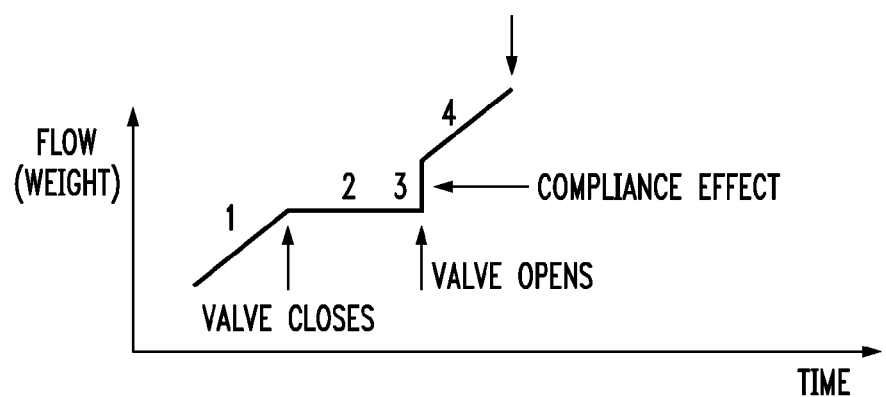
Figure 9G:
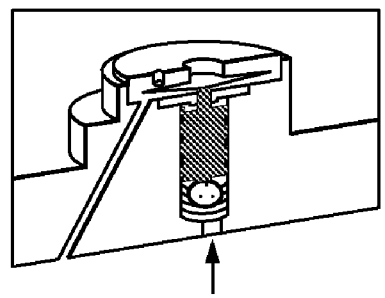
Figure 9G:
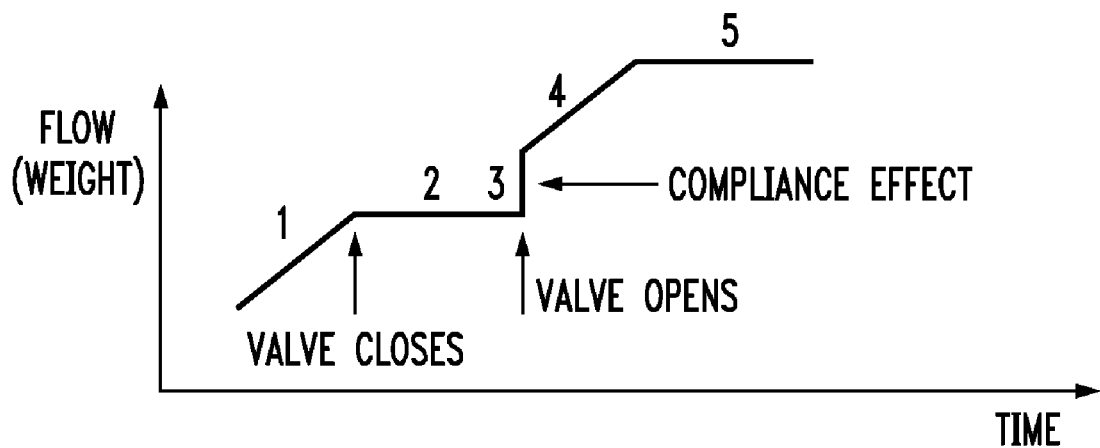

The compliance effect due to the compressible seal 26 can be explained by analogy to an air bubble lodged in a valve. FIGS. 9*a*-9*g* depict this air bubble example. In FIG. 9*a*, the valve is open and the air bubble is at its lowest pressure. A constant flow rate will be dispensed from the valve as illustrated by that portion of the graphical waveform having a substantially constant slope (segment "1"). FIG. 9*b* shows the valve immediately after transitioning from an OPENED state to a CLOSED state. Once the valve is closed a fixed or unchanging flow rate is experienced (as denoted by the substantially horizontal waveform, e.g., segment "2"), as shown in FIG. 9c. While the valve is in this CLOSED state, pressurized fluid from the reservoir compresses against thereby reducing in size the air bubble (FIG. 9c). Accordingly, the pressure in the air bubble is greater when the valve is in a CLOSED state than when the valve is in an OPENED state. Lastly, FIG. 9d depicts the reopening of the valve. Since the bubble was in a compressed state when the valve was closed, upon opening the valve the bubble must first return to its decompressed or equilibrium state. This decompression is represented by the vertical portion of the waveform (segment "3") in FIG. 9d. Although depicted as a vertical segment, in actuality such decompression or equilibrium occurs extremely quickly over a relatively short period of time. During decompression undesirably some unaccounted for fluid will be dispensed from the outlet passage 22 of the fluidic delivery device thereby compromising the accuracy of the flow rate. Once the pressure has been equalized, then the fluid will once again be dispensed from the outlet passage 22 at a substantially constant flow rate, as represented by the graphical portion of the waveform having a constant slope (segment "4") in FIG. 9e. This compliance effect is produced each time the valve transitions from a CLOSED state to an OPEN state. Lastly, FIG. 9f depicts the transitioning of the valve from the OPENED state to the CLOSED state, whereby the air bubble is once more compressed in size due to the pressurized fluid from the reservoir. A fixed or unchanging flow rate is experienced (as denoted by the substantially horizontal waveform, e.g., segment "5"), as shown in FIG. 9g, while the valve is in the CLOSED state.

Figure 8:
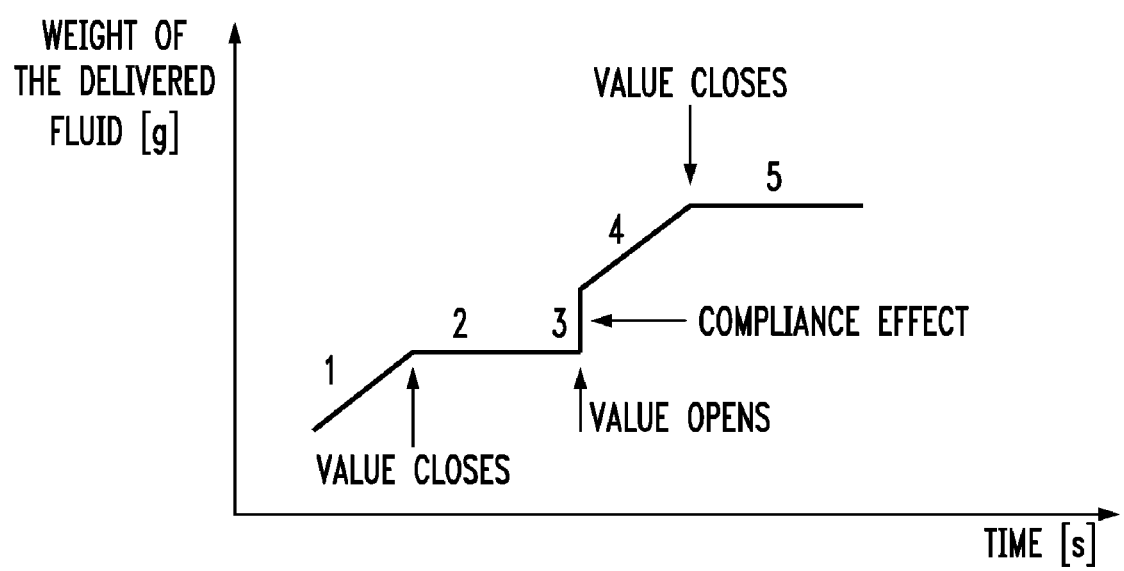
FIG. 8 is a graphical representation of the weight of fluid delivered by a fluidic delivery device over time showing the compliance effect produced by the seal.

There is no air bubble in a valve assembly. Instead, the air bubble example shown in FIGS. 9a-9g is merely an illustrative tool for understanding what in actuality occurs in the valve assembly 10 shown in FIG. 1b wherein the compressible seal 26 produces a similar compliance effect. Every valve in which a compressible material is in contact with a rigid material will result in an analogous compliance effect. The compressible material, that is, seal 26 in FIG. 1b, is likened to the air bubble in the example described above in FIGS. 9a-9f Referring once again to the graphical waveform depicted in FIG. 8, when the valve is in an OPENED state seal 26 is at its lowest pressure. A constant flow rate will be dispensed from the valve as illustrated by segment "1" of the waveform (FIG. 8) having a substantially constant slope. If the valve is closed, the pressurized fluid from the reservoir 62 compresses the seal 26 downward into the bore 14. Accordingly, the pressure applied across the seal 26 is greater when the valve is in a CLOSED state than when the valve is in an OPEN state. While the valve is closed the flow rate of fluid dispensed from the valve remains unchanged as represented by the horizontal portion of the graphical waveform (segment "2") in FIG. 8. Thereafter, the valve is reopened (segment "4"). Since the seal 26 was in a compressed state when the valve was closed as a result of the pressurized fluid in the reservoir, upon opening the valve the seal 26 first returns to its decompressed or equilibrium state. This decompression is represented by vertical segment "3" of the waveform in FIG. 8 and depicts the compliance effect. Although depicted as a vertical waveform, in actuality such decompression or equilibrium occurs extremely quickly over a relatively short period of time. During decompression of the seal 26 some accounted for fluid is disadvantageously dispensed from the outlet passage 22 thereby resulting in an overdosage and compromising the overall flow rate accuracy. Once the pressure has been equalized, then the fluid will be dispensed from the outlet passage 22 at a substantially constant flow rate, once again as represented by segment "4" of the waveform having a constant slope in FIG. 8. Segment "5" of the waveform in FIG. 8 shows the valve once again in a CLOSED state as denoted by the substantially horizontal waveform whereby the seal 26 is compressed downward due to the pressurized fluid from the reservoir 62.

The compliance effect resulting from decompression of the seal 26 when transitioning from a CLOSED state to an OPEN state will disadvantageously dispense an overdosage of fluid relative to the fluid dosage in the fluid delivery profile programmed by the user. As a result of this overdosage, the accuracy of the flow rate dispensed from the fluidic delivery device will be diminished or compromised. The present invention compensates, corrects or adjusts for the overdosage resulting from the compliance effect of the seal 26 thereby improving the flow rate accuracy of the fluidic delivery device.

In addition to the compliance effect caused by the compressible seal 26, other factors may also adversely affect the accuracy of the flow rate of the fluidic delivery device and may differ among fluidic delivery devices. One such factor is the maximum flow rate for a given fluidic delivery device, which is dependent on: (a) the fluidic regulator or fluidic restrictor, and (b) the differential pressure across the fluidic regulator or fluidic restrictor. Both of these parameters may differ among fluidic delivery devices. The fluidic regulator or fluidic resistor 60 (as shown in FIG. 1b) may be selected to achieve a desired flow rate. As for the differential pressure across the fluidic restrictor, this value may be determined by subtracting the ambient pressure from the reservoir pressure. Once again the reservoir pressure may vary among fluidic delivery devices. Variation in reservoir fluid pressure will impact the maximum flow rate of fluid delivered by the fluidic delivery device. Any deviation in maximum flow rate, in turn, will compromise the accuracy of the programmed flow rate of the fluid being dispensed from the fluidic delivery device.

Yet another parameter that has an impact on the accuracy of the flow rate for a particular fluidic delivery device is the dependency temperature has on the pressure of the fluid in the reservoir. As the temperature increases, the reservoir pressure increases, therefore the flow rate will increase. Here again, any change in flow rate will diminish the flow rate accuracy of the fluid delivered from the fluidic delivery device at a programmed fluid delivery profile.

Any given fluidic delivery device will also have an associated valve OPENING time (time required for the piezoelectric actuator to reach the valve OPENING voltage, reference element 302 in FIG. 3c) and valve CLOSING time (time required for the voltage across the piezoelectric actuator to drop from the 60V predetermined threshold voltage to the valve OPENING voltage, reference element 302 in FIG. 3c) that may vary among fluidic delivery devices. For instance, two fluidic delivery devices may be programmed to have the same fluid delivery profile but different valve OPENING voltages (represented by reference element 302 in FIG. 3c) and associated valve OPENING times. For instance, a first fluidic delivery device may have a valve OPENING voltage of 57V while a second fluidic delivery device has a valve OPENING voltage of 55V. A longer valve OPENING time (i.e., time for charge across the piezoelectric actuator to reach the valve OPENING voltage) will be required for the first fluidic delivery device to reach the associated first valve OPENING voltage of 57V in comparison to the valve OPENING time for the second fluidic delivery device needed to attain the associated second valve OPENING voltage of 55V. The longer the valve OPENING time required to reach the associated valve OPENING voltage, the longer the time needed for the valve to remain in a valve OPENED state. Accordingly, transistor 620 in FIG. 4 will have to be driven (e.g., switched ON/OFF) by the PWM charge input signal for a longer duration of time. In summary, the valve OPENED time varies as a direct function of the valve OPENING time. That is, as the vale OPENING time increases, the duration of time for which the valve needs to remain in an OPENED state to reach the predetermined threshold voltage of 60V also increases. Therefore, if the time for which the valve needs to remain in an OPENED state is not adjusted or compensated for accordingly depending on the valve OPENING voltage and associated valve OPENING time for the particular fluidic delivery system, then undesirably an underdosage of fluid will be dispensed or delivered thereby comprising the accuracy of the flow rate.

The present invention optimizes the flow rate accuracy of the fluidic delivery device by compensating for any one or more of these fluidic parameters. During manufacture of the valve assembly, one or more fluidic parameters (e.g., compliance effect, maximum flow rate, temperature-pressure relationship of reservoir fluid, valve OPENING time, and valve CLOSING time) that could have an impact on the accuracy of the flow rate is quantified or calibrated preferably for each particular valve assembly. Alternatively, instead of calibrating one or more fluidic parameters for each valve assembly a constant or fixed calibrated value may otherwise be used for all valve assemblies resulting in a less accurate flow rate. As still another alternative to specifically calibrating the fluidic parameter, an approximation may be utilized by relying on other known parameters that need not be calibrated. Hereinafter these fluidic parameters calibrated at the time of manufacture are collectively referred to as the "calibrated fluidic parameters" and stored in a memory associated with the fluidic delivery device, preferably a non-volatile memory such as a FLASH memory, described in detail below.

Specifically, the compliance effect for a particular valve assembly may be quantified or calibrated by measuring the change in weight of delivered fluid from the valve assembly ($\Delta y$ of segment "3" in FIG. 8) as a result of the compliance effect when transitioning the valve from a CLOSED state to an OPENED state. Alternatively, instead of measuring the weight of the dispensed fluid, the volume may be monitored based on the time needed to fill a predefined volume when operating at a constant flow rate. In either case, the weight or volume of the fluid dispensed as a result of the compliance effect due to the seal 26 can be quantified through testing and stored in memory. The maximum flow rate may be calibrated by merely operating the valve and monitoring how long it takes to fill a predefined volume. A temperature-pressure relationship of the reservoir fluid may be established by monitoring the pressure of the fluid in the reservoir while varying the temperature. Lastly, the valve OPENING time of the valve assembly is dependent on the valve OPENING voltage and may be calibrated by monitoring the period of time it takes the piezoelectric actuator to reach the valve OPENING voltage. The present invention is not limited to these described methods for ascertaining the calibrated fluidic parameters and other methods are contemplated. As previously mentioned, once calibrated, these fluidic parameters are stored in memory, preferably a non-volatile memory, associated with the fluidic delivery device.

Using a control device a user (e.g., patient, clinician, technician, nurse, physician) programs the fluidic delivery device to dispense a fluid over time based on a programmed fluid delivery profile. The fluid delivery profile is preferably for a 24 hour period subdivided into one or more time intervals, each time interval being a multiple of one hour increments of desired duration. Each time interval is preferably less than or equal to a maximum time interval (preferably 24 hours) but greater than or equal to a minimum time interval (preferably one hour). For instance, the 24 hour fluid delivery profile may be subdivided into 24 time intervals, each time interval 1 hour in duration. Alternatively, the 24 hour fluid delivery profile may be subdivided into 4 time intervals, each time interval 6 hours in duration. Still yet another exemplary 24 hour fluid delivery profile may comprise only 2 time intervals, the first time interval being 1 hour in duration, while the last time interval is 23 hours. As is evident from these examples, the 24 hour fluid delivery profile may be subdivided so that the time intervals are of equal or unequal duration. Furthermore, the minimum time interval and maximum time interval may also be programmed, as desired. In addition to the time intervals, the user also programs the concentration and delivery rate of the fluid to be delivered by the fluidic delivery device.

Once a fluid delivery profile has been programmed or configured by a control device communication is established, preferably via a wireless communication interface, with the fluidic delivery device. Initially, the control unit reads any one or more of the calibrated fluidic parameters stored in a non-volatile memory device associated with the fluidic delivery device. The control device calculates, for each time interval of the 24 hour fluid delivery profile, two values. A first value referred to as an Integer Compensated Valve OPENING Time Per Block (e.g., 400 second block) over a particular time interval. The second value computed is hereinafter referred to as a Remainder Compensated Valve OPENING Time Per Hour. For a particular time interval, these two values are calculated by the control device based on the flow rate programmed by the user over that particular time interval and one or more calibrated fluidic parameters.

An illustrative example will be described wherein the 24 hour programmed fluid delivery profile is divided into 8 time intervals, each time interval being 3 hours in duration. The block is set to 400 seconds in duration, during which a portion of time the valve remains in an OPENED state and for the remaining portion of time is in a CLOSED state.

Figure 10:
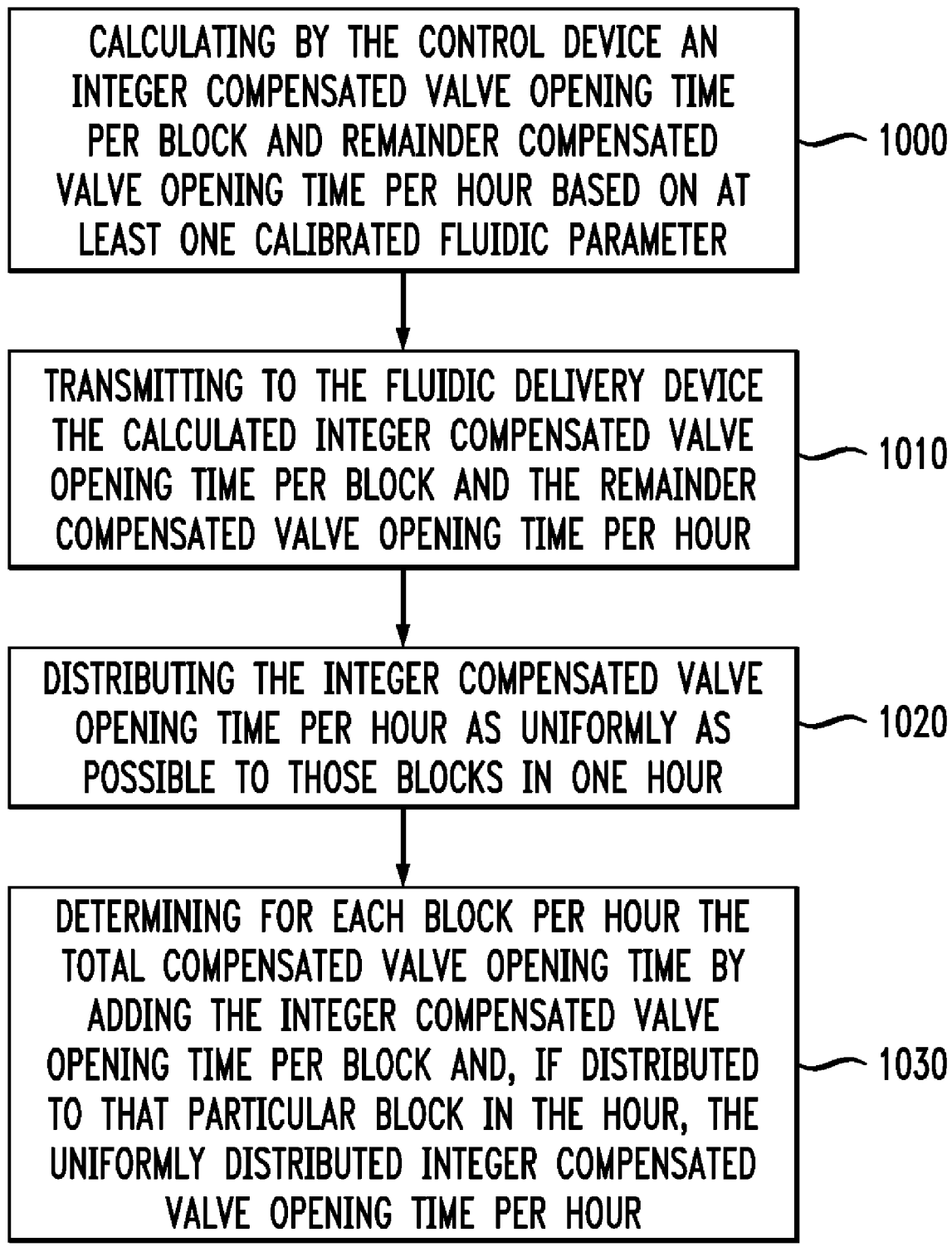
FIG. 10 is an exemplary flow chart depicting the process in determining the Total Compensated Valve OPENING Time Per Block to compensate for one or more of the calibrated fluidic parameters.

FIG. 10 is an exemplary flow diagram of the steps performed by the fluidic delivery system (FIG. 11) in adjusting the valve OPENING time (i.e., time needed for the piezoelectric actuator to reach a valve OPENING voltage, reference element 302 in FIG. 3c) to compensate for any overdosage or underdosage of fluid delivery due to the impact one or more of the calibrated fluidic parameters. In step 1000, processor 1110 associated with the control device 1105 will determine two values: (i) an Integer Compensated Valve OPENING Time Per Block and (ii) a Remainder Compensated Valve OPENING Time Per Hour.

The Compensated Valve OPENING Time Per Hour is calculated by performing an Integer operation on the summation of Compensation Components associated with any one or more of the fluidic parameters. The Compensated Valve OPENING Time Per Hour compensating for all five fluidic parameters is represented by the Equation (1) below:

Integer Compensated Valve OPENING Time Per Block=Integer (Maximum Flow Rate Compensation Component+Valve OPENING Time Compensation Component+Valve CLOSING Time Compensation Component+Compliance Effect Compensation Component+Temperature-Pressure Relationship Compensation Component))   Equation (1)

The Compensation Component for each fluidic parameter will be addressed separately.

The Maximum Flow Rate Compensation Component= (programmed flow rate/calibrated maximum flow rate)*Duration of Block wherein, programmed flow rate—is programmed by the user (e.g., physician, technician, nurse, patient). This value may be entered by the user directly as a predetermined volume/day (e.g., mL/day) or indirectly as a weight to be delivered/day (e.g., mg/day), whereby the programmed flow rate may be determined by dividing the weight to be delivered per day by the specified drug concentration level programmed by the user.

calibrated maximum flow rate—calibrated at the time of manufacture of the fluidic delivery device and stored in the non-volatile memory associated with the fluidic delivery device . The maximum flow rate represents the flow rate delivered by the valve when continuously open (e.g., see FIG. 2a). Typically, the maximum flow rate is in the range of approximately 3.7 mL/day-4.3 mL/day).

Duration of Block—is the duration of time in which the valve is opened once and closed once (e.g., 400 seconds).

The next three Compensations Components (e.g., Valve OPENING Time Compensation Component, Valve CLOSING Time Compensation Component and Compliance Effect Compensation Component) in Equation (1) will now be addressed together. Each of these three Compensation Components may be specifically calibrated for each fluidic delivery device. With negligible compromise to the accuracy of the flow rate, rather than specifically calibrating each of these three Compensation Components for each fluidic delivery device, a constant value may be established for each of these three Compensation Components and utilized for all fluidic delivery devices. Yet a third approach may be employed as an alternative to specifically calibrating the three Compensation Components for each fluidic delivery device, whereby a known value is used as the Compensation Component. For instance, the rise time for the charge applied across the piezoelectric actuator to reach the predetermined threshold voltage of 60V is a known value with negligible difference compared with the calibrated valve OPENING time and thus may be utilized as the calibrated valve OPENING time to eliminate having to perform this additional calculation. Each of these three Compensation Components are also stored in a non-volatile memory associated with the fluidic delivery device at the time of manufacture. It is noted that the compliance effect will result in an overdosage of fluid delivered by the fluidic delivery device and thus the Compliance Effect Compensation Component is a negative value to reduce the valve OPENING time, while the valve OPENING time and valve CLOSING time will result in an underdosage so the respective Compensation Component for each is a positive value.

Referring once again to Equation (1) the last fluidic component to be addressed is the Temperature-Pressure Relationship Compensation Component. At the time of manufacture, the temperature-pressure relationship of fluid in the reservoir is characterized to determine its impact on the flow rate and a temperature dependent function is established as the Temperature-Pressure Relationship Compensation Component.

The other value calculated by the control device is the Remainder Compensated Valve OPENING Time Per Hour by performing a MODULUS mathematical operation on (summation of the Compensation Component for one or more of the fluidic parameters, each Compensation Component being multiplied by the Number of Blocks in One Hour), Number of Blocks in One Hour). The Remainder Compensated Valve OPENING Time Per Hour compensating for all five fluidic parameters is represented by the Equation (2) below:

Remainder Compensated Valve OPENING Time Per Hour=MOD ((((Maximum Flow Rate Compensation Component)*Duration of the Block*Number of Blocks in One Hour)+(Valve OPENING Time Compensation Component*Number of Blocks in One Hour )+(Valve CLOSIGN Time Compensation Component*Number of Blocks in One Hour )+(Temperature-Pressure Relationship Compensation Component*Number of Blocks in One Hour)), Number of Blocks in One Hour)   Equation (2)

The same variables in Equation (2) were also found in the Equation (1) and described above when calculating the Integer Compensated Valve OPENING Time Per Block and thus need not be described further.

In step 1010 of FIG. 10, the Integer Compensated Valve OPENING Time Per Block and the Remainder Compensated Valve OPENING Time Per Hour calculated by the control device are transmitted to the fluidic delivery device via a communication interface. The fluidic delivery device receives the Integer Compensated Valve OPENING Time Per Block and applies it to every block in that time interval. However, in step 1020 the Remainder Compensated Valve OPENING Time Per Hour is distributed by the fluidic delivery device to those blocks within one hour such that it is as uniform as possible wherein the time distributed to any particular block is a whole number (non-negative integer) of one or more seconds. On the one hand, if the Remainder Compensated Valve OPENING Time Per Hour is a whole number that is equally divisible among the total number of blocks in one hour without a remainder then the Remainder Compensated Valve OPENING Time Per Hour is divided by the number of blocks per hour and distributed equally to each block. On the other hand, if the Remainder Compensated Valve OPENING Time Per Hour is a whole number that is not equally divisible among the total number of blocks in one hour without a remainder, it is distributed as uniformly as possible as a whole number of one or more seconds among less than all the blocks within the one hour. For each block within one hour over the given time interval, in step 1030, the Total Compensated Valve OPENING time is computed by adding the Integer Compensated Valve OPENING Time Per Block plus, if distributed to that particular block, the Remainder Compensated Valve OPENING time per hour.

By way of example, the valve OPENING time will be compensated for only three of the four fluidic parameters, namely, compliance effect, maximum flow rate and valve OPENING time/valve CLOSING time. The temperature-pressure dependency of the fluid in the reservoir is not compensated for in this example.

One hour of time is divided into 9 blocks, each block 400 seconds in duration.

Control device 1105 retrieves from the non-volatile memory (e.g. FLASH memory) associated with the fluidic delivery device three calibrated parameters: compliance effect, maximum flow rate and valve OPENING time. These values are processed by the control unit to generate an Integer Compensated Valve OPENING Time Per 400 Second Block calculated using the following equation:

Integer Compensated Valve OPENING Time Per 400 Second Block=Integer ((Maximum Flow Rate Compensation Value)*400+Valve Net Compensation Component)

and, a Remainder Compensated Valve OPENING Time Per Hour calculated using the following equation:

Remainder Compensated Valve OPENING Time Per Hour=MOD ((((Maximum Flow Rate Compensation Component)*400*9)+(Valve Net Compensation Component*9)), 9)

As discussed above with respect to Equations (1) & (2), the Maximum Flow Rate Compensation Component=(programmed flow rate/calibrated maximum flow rate)*Duration of Block.

The Valve Net Compensation Component in this example represents the summation of the Valve OPENING Time Compensation Component, the Valve CLOSING Time Compensation Component and the Compliance Effect Compensation Component. In this example each of these three Compensation Components is represented as a constant value, rather than being specifically calibrated for each fluidic delivery device, and thus have been combined into a single constant value referred to as Valve Net Compensation Component.

Assuming the programmed flow rate is 0.5 mL/day, the calibrated maximum flow rate is 3.95 mL/day and the calibrated Valve Net Compensation is 5 seconds, then the calculated Integer Compensated Valve OPENING Time Per 400 Second Block=Integer ((0.5/3.95)*400+5)=55 seconds. The Remainder Compensated Valve OPENING Time Per Hour=MOD (((0.5/3.95)*400*9)+(5*9)),9)=5 seconds. Since the Remainder Compensated Valve OPENING Time Per Hour of 5 seconds is not evenly divisible by 9 (the number of 400 second blocks in one hour), then the 5 seconds will be distributed in one second intervals over the 9 blocks as uniformly as possible. Specifically, the 5 seconds will be uniformly distributed across 5 out of the 9 blocks over one hour so each of the 5 blocks has an additional one second. The Total Compensated Valve OPENING Time Per Hour is then determined for each of the 9 blocks over one hour based on the Integer Compensated Valve OPENING Time Per Block (applied to each block) and the Remainder Compensated Valve OPENING Time Per Hour (if distributed to that particular block). A Total Compensated Valve OPENING Time for 4 of the 9 blocks will be set to 55 seconds while 5 of the 9 blocks will be set to 56 seconds (55 seconds+1 second).

In another example, the Integer Compensated Valve OPENING Time Per Block is calculated as 111 seconds and the Remainder Compensated Valve OPENING Time Per Hour is 9 seconds. Since the Remainder Compensated Valve OPENING Time Per Hour (e.g., 9 seconds) is evenly divisible without a remainder by the number of blocks per hour (9 blocks), each of the 9 blocks in one hour will have a Remainder Compensated Valve OPENING Time Per Hour of 1 second. Thus, each of the 9 blocks over one hour will have a Total Compensated Valve OPENING time of 112 seconds (111 seconds +1 second).

Figure 11:
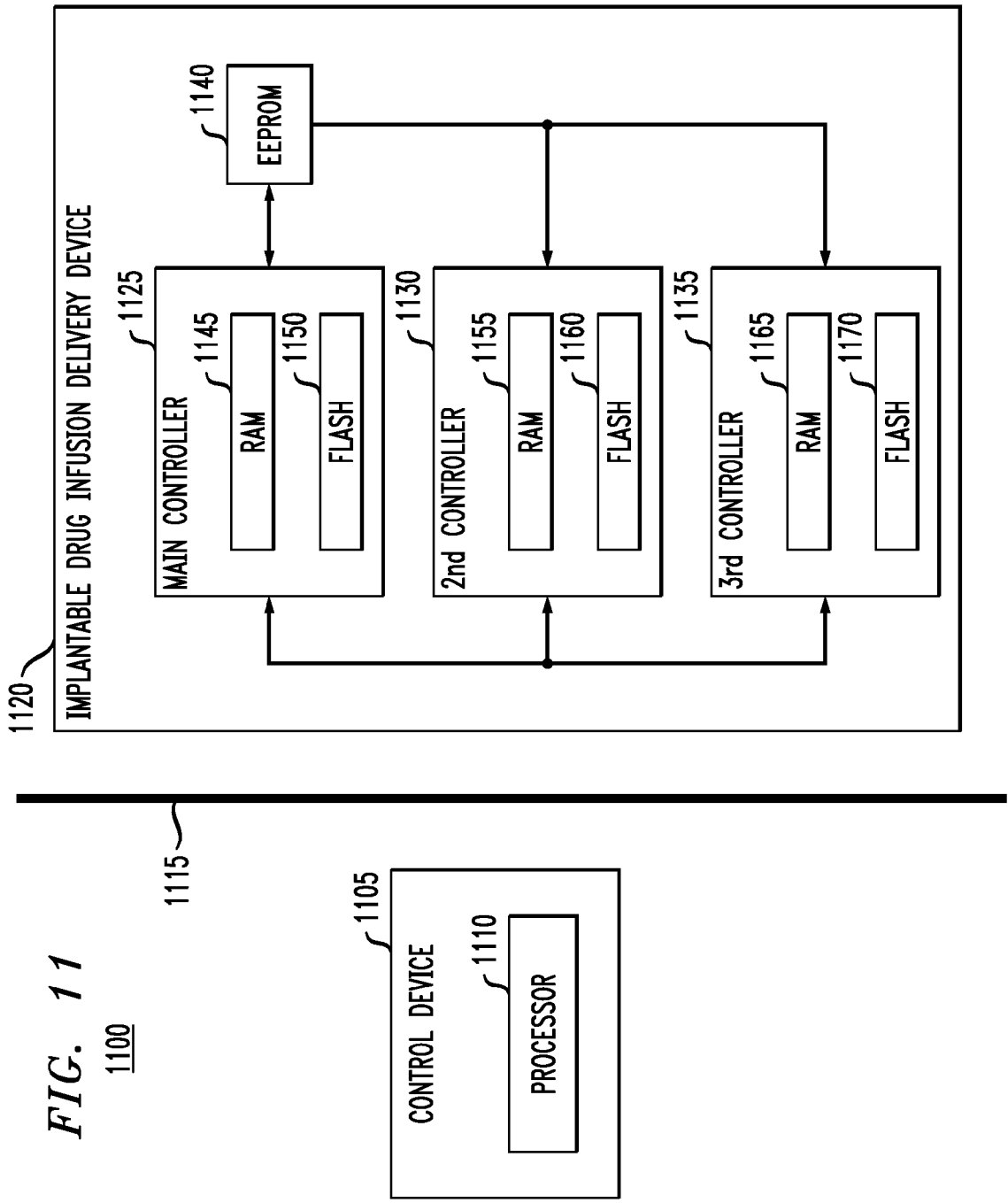
FIG. 11 is an exemplary schematic diagram of an external control device used to program an implantable drug delivery device and the specific memory architecture within the implantable drug delivery device.

The invention described thus far is directed to improving the accuracy of the programmed flow rate for a fluidic delivery device. In keeping with this goal it is important to monitor any inconsistencies in programming of the fluidic delivery device. To mitigate the risk of incorrectly programming the fluidic delivery device, the control unit preferably verifies the consistency of the data transmitted to the fluidic delivery device before programming the fluidic delivery device. As discussed in detail above, the Integer Compensated Valve OPENING Time Per Block (Equation (1)) and Remainder Compensated Valve OPENING Time Per Hour (Equation (2)) are both calculated by the control device based on the fluidic calibration parameters stored in a non-volatile memory associated with the fluidic delivery device. The source code programming steps for each of these two equations is provided twice or duplicated in the programming code for processor 1110 (FIG. 11). The first iteration or calculation of Equations (1) and (2) is performed using a first portion of the programming source code. Before programming the fluidic delivery device, the control device verifies that these same two values are obtained by recalculating Equations (1) and (2) using source code programming steps set forth in a second portion of the programming source code, different from the first portion. This redundant processing mitigates the risk of a programming failure by verifying the flow data integrity prior to transmission.

In order to further reduce the risk of incorrectly programming the fluid delivery device, additional checks may be performed using a specific memory architecture as shown in FIG. 11 for the fluidic delivery system 1100. System 1100 includes an implantable drug infusion delivery device 1120 programmed by an external control device 1105 via a wireless communication interface. Implantable drug infusion delivery device 1120 includes three controllers or processors 1125, 1130, 1135, however, any number of one or more controllers or processors may be used, as desired. Each controller has associated therewith a volatile memory device such as a RAM and a non-volatile memory device, for example, a FLASH memory. A first, primary or main controller 112 has a volatile RAM memory 145 and a non-volatile FLASH memory 1150. Any number of one or more secondary or auxiliary controllers may be included. In the example, there are two secondary or auxiliary controllers, e.g., a second controller 1130 and a third controller 1135. Similar to the primary, first or main controller 1125, each secondary or auxiliary controller 1130, 1135 also has a volatile RAM and a non-volatile FLASH memory. Also associated with the implantable drug infusion delivery device 1120 but external to the controllers 1125, 1130, 1135 is a non-volatile EEPROM 1140 electrically connected to the main controller 1125.

The calibrated fluidic parameters (e.g., compliance effect, maximum flow rate, temperature-pressure relationship of reservoir fluid and opening voltage rise time) are stored in the non-volatile FLASH memory 1150 associated with the main controller 1125. The values calculated by the control device (e.g., the Integer Compensated Valve OPENING Time Per Block and the Remainder Compensated Valve OPENING Time Per Hour) are received by the implantable drug infusion delivery device 1120 and stored in the non-volatile EEPROM memory 1140 associated therewith.

During self-testing, preferably once a day, the implantable drug infusion delivery device 1120 calculates a FLASH code memory CRC and compares this calculated value with the FLASH code memory CRC that was previously stored in the FLASH memory 1150 when the implantable drug infusion delivery device 1120 was programmed during manufacturing. If the calculated CRC doesn't match with the previously stored CRC value for the FLASH code memory, then a FLASH code error is set, an alarm is engaged and delivery of the drug ceases. This process allows checking for corruption of the fluid calibration parameters stored in the non-volatile FLASH memory 1150.

In order to minimize power consumption, the main controller 1125 is powered off until awakened when required to perform processing. Whenever the main controller wakes up it copies the entire contents of the non-volatile EEPROM memory 1140 to volatile RAM memory 1145. When reading the contents of the EEPROM memory 1140, the main controller 1125 calculates the EEPROM checksum and verifies it with the previously stored checksum in the EEPROM memory. If the calculated checksum doesn't match with the previously stored checksum in the EEPROM, then the EEPROM error code is set, an alarm is engaged and drug delivery ceases. Such verification processing will detect corruption of the fluid delivery profile since the Integer Compensated Valve OPENING Time Per Block and the Remainder Compensated Valve OPENING Time Per Hour for every time interval comprising the fluid delivery profile is stored in EEPROM memory 1140.

Upon a reset event triggered by any of the controllers, the other secondary controllers (other than the main controller 1125) also copy the drug delivery profile data from the EEPROM 1140 into their respective associated RAM, either via a direct path (e.g., EEPROM directly to RAM associated with secondary controller) or through an indirect path (e.g., EEPROM to RAM associated with main controller to RAM associated with secondary controller).

As explained above, the EEPROM 1140 and the secondary controllers (other than the main controller 1125) commonly store the same drug delivery profile data in their respective RAM memories. The drug delivery profile data is stored in the EEPROM 1140 of the main controller 1125 because it receives the information from the control device 1105. For instance, the main controller 1125 programs the second controller 1130 with the same drug delivery profile, because the second controller 1130 drives the valve. The same drug delivery profile is stored in the third controller 1135 as well. During daily self-testing of the implantable drug infusion delivery device 1120, the drug delivery profile data is stored in the EEPROM 1140 as well as in the volatile RAM associated with each of the controllers. If during self-testing there is a discrepancy between the drug profile data stored in EEPROM 1140 and that stored in any of the volatile RAMs of any of the controllers, an alarm will be activated and drug delivery will cease.

Any of the previously described methods may be employed separately or used in any combination thereof for mitigating the risk of delivery of the fluid from the fluidic delivery device at an incorrect flow rate. In the first instance, the fluid delivery profile data is verified prior to programming the fluidic delivery device, whereas the second additional method checks the consistency of the fluid delivery device profile stored in the memory associated with the fluidic delivery device, preferably at least once a day.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A valve assembly with optimized flow rate accuracy over its lifetime, comprising:
    a power supply;
    charge pump circuitry powered by the power supply;
    a piezoelectric actuator charged by the charge pump circuitry, the charge applied across the piezoelectric actuator reaching a predetermined threshold voltage over a rise time; and
    a valve transitioning from a CLOSED state to an OPEN state when the piezoelectric actuator exceeds the predetermined threshold voltage; the charge pump circuitry receives as input a PWM charge input signal subdivided into a plurality of PWM units, together comprising a PWM group, each of the plural PWM units having its own associated PWM parameters applied to that PWM unit so as to minimize a valve OPENING time and optimize the flow rate accuracy over the lifetime of the valve.

2. The valve assembly in accordance with claim 1, wherein each of the plural PWM units in the PWM group are equal in duration.

3. The valve assembly in accordance with claim 1, wherein the plural PWM units in the PWM group are not all equal in duration.

4. The valve assembly in accordance with claim 1, wherein the charge pump circuitry comprises a transistor electrically connected to an inductor.

5. The valve assembly in accordance with claim 4, the PWM charge pump input signal being generated by a processor is received as input to the transistor for establishing transistor ON time when the PWM charge pump input signal is high and transistor OFF time when the PWM charge pump input signal is low.

6. The valve assembly in accordance with claim 5, wherein when the power supply is substantially constant, among the plural PWM units in a particular PWM group, the transistor ON time remains constant, while the transistor OFF time is varied over time due to increasing charge built up across the piezoelectric actuator.

7. The valve assembly in accordance with claim 6, wherein with depleting voltage supplied by the power supply over time, among the plural PWM units in a particular PWM group, the transistor OFF time remains constant, while the transistor ON time is varied over time to compensate for the depleting voltage supplied by the power supply.

8. The valve assembly in accordance with claim 5, wherein with depleting voltage supplied by the power supply over time, among the plural PWM units in a particular PWM group, the transistor OFF time remains constant, while the transistor ON time is varied over time to compensate for the depleting voltage supplied by the power supply.

* * * * *